United States Patent [19]
Kelly et al.

[11] Patent Number: 5,332,837
[45] Date of Patent: Jul. 26, 1994

[54] CC-1065 ANALOGS

[75] Inventors: Robert C. Kelly, Augusta; David G. Martin, Kalamazoo; Paul A. Aristoff, Portage, all of Mich.

[73] Assignee: The Upjohn Company, Kalamazoo, Mich.

[21] Appl. No.: 10,526

[22] Filed: Jan. 22, 1993

Related U.S. Application Data

[63] Continuation of Ser. No. 845,762, Mar. 2, 1992, abandoned, which is a continuation of Ser. No. 674,422, Mar. 22, 1991, abandoned, which is a continuation of Ser. No. 554,931, Jul. 18, 1990, abandoned, which is a continuation of Ser. No. 382,159, Jun. 8, 1989, abandoned, which is a continuation of Ser. No. 944,633, Dec. 19, 1986, abandoned.

[51] Int. Cl.$^5$ ............... C07D 487/04; C07D 487/08; A61K 31/40
[52] U.S. Cl. .................... 548/433; 548/421; 435/119; 435/169
[58] Field of Search ............... 548/421, 433, 159, 181, 548/217, 305.1; 435/119, 169; 544/355, 405; 546/168, 271; 514/249, 253, 314, 338, 365, 367, 375, 394, 411

[56] References Cited

U.S. PATENT DOCUMENTS 4,912,227 3/1990 Kelley .................. 548/421

FOREIGN PATENT DOCUMENTS 154445 2/1985 European Pat. Off. .

OTHER PUBLICATIONS

Burger, A. "A guide to the chemical basis of drug design" John Wiley & Sons, N.Y. 1984 p. 15.
Korolkovas, A. Essentials of Medicinal Chemistry. 2nd ed. (1988). John Wiley & Sons:New York. pp. 102–103.
Bundgaard, H. (Ed.). Design of Prodrugs. (1985). Elsevier:Amsterdam. pp. 1–9.
Sinkula, A. A. and S. H. Yalkowsky. "Rationale for Design of Biologically Reversible Drug Derivatives: Prodrugs," Journal of Pharmaceutical Sciences, 64:2 (Feb. 1975), 181–210.
Sinkula, A. A. "Prodrug Approach in Drug Design," Ann. Rep. Med. Chem., 10 (1975), 306–316.

Primary Examiner—C. Warren Ivy
Assistant Examiner—Celia Chang

[57] ABSTRACT

This invention concerns 2-acyl-4,5,8,8a-tetrahydro-4-oxycyclopropan[c]pyrrol(3,2-e) indole derivatives of Formula I':

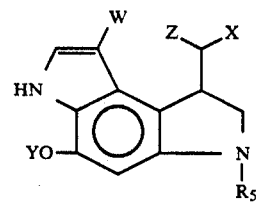

the compounds of Formula I' are useful as uv light absorber substances, as chemical intermediates and as prodrugs of known spirocyclopropylpyrroloindole CC-1065 analogs. Representative Formula I' compounds have been shown to possess useful ranges of antitumor activity in standard laboratory animal tests.

20 Claims, No Drawings

CC-1065 ANALOGS

CROSS REFERENCE TO RELATED APPLICATIONS

This application is a continuation of U.S. Ser. No. 07/845,762 filed 02 March 1992, now abandoned; which is a continuation of U.S. Ser. No. 07/674,422 filed 22 Mar. 1991, now abandoned; which is a continuation of U.S. Ser. No. 07/554,931 filed 18 Jul. 1990, now abandoned; which is a continuation of U.S. Ser. No. 07/382,159 filed 8 Jun. 1989, now abandoned; which is the national phase of PCT/US87/03227 filed 11 Dec. 1987; which is a continuation of U.S. Ser. No. 06/944,633 filed 19 Dec. 1986, now abandoned.

BACKGROUND OF THE INVENTION

Antibiotic CC-1065, (7bR,8aS)-7-[[1,6-dihydro 4-hydroxy-5-methoxy-7-[(4,5,8,8a-tetrahydro-7-methyl-4-oxocyclopropa[c ]pyrrolo[3,2-e]indol-2(1H)-yl)carbonyl]benzo[1,2-b:4,3-b']dipyrrol-3(2H)-yl]carbonyl]1,6-dihydro-4-hydroxy-5-methoxy-benzo[1,2-b:4,3-b']dipyrrole-3(2H)-carboxamide, is disclosed and claimed in L. J. Hanka et al U.S. Pat. No. 4,169,888 together with a process for preparing antibiotic CC-1065 by aerobic fermentation procedures, and recovering antibiotic CO-1065 therefrom.

In The Journal of Antibiotics, 1985, 38, 746, D. G. Martin et al reported that acetic acid adds across the spirocyclopropylcyclohexadienyl (SCPCH) system of CC-1065 to produce the phenolic, acetic acid product (AAP), 7-[[7-[[1-[(acetyloxy)methyl]-1,6-dihydro-5-hydroxy-8-methylbenzo[1,2-b:4,3-b']dipyrrol-3(2H)-yl]carbonyl]-1,6-dihydro-4-hydroxy-5-methoxybenzo[1,2-b:4,3-b']-dipyrrol-3(2H)-yl]carbonyl]-1,6-dihydro-4-hydroxy-5-methoxy-benzo[1,2-b:4,3-b']dipyrrole-3(2H)-carboxamide. AAP was tested in vitro and in vivo and found to be less potent than CC-1065 by a factor of $10^3$ to $10^4$ depending upon the particular test system and therefore tended to divert attention from adducts of the SCPCH system as useful antitumor agents or as prodrugs to CC-1065 analogs.

In J. Am. Chem. Soc., 103, No. 18, 1981, W. Wierenga published a "Synthesis of the Left-Hand Segment of the Antitumor Agent CC-1065".

EP Application 0 154 445 (published 11.09.85) discloses various analogs of antibiotic CC-1065, including compounds of formula EP-I and EP-II (see General Formula chart of EP 0154 445), wherein $R_1$ in formula EP-II is $CH_3$—, —$CH_2Ph$, CH=$CHCH_2$—, —$CH_2SCH_3$, —$CH_2OCH_3$, —$CH_2OCH_2CH_2OCH_3$, —$CH_2CCl_3$, —$CH_2CH_2Si(R_2)_3$, or H, where Ph is phenyl; R is alkyl($C_1$-$C_5$), phenyl, or H; $R_2'$ is $C_1$ to $C_5$-alkyl, phenyl or hydrogen, and is not necessarily the same as R in one compound; $R_3$ is alkyl($C_1$-$C_5$), phenyl, or H; and X is Cl, Br, or I-, or $OSO_2R_4O$, where $R_{40}$ is $C_1$ to $C_5$-alkyl, phenyl, tolyl, bromophenyl, nitrophenyl, or trifluromethyl. The O-protected compounds of formula EP-II are chemically stable and only removable under specific chemical conditions. However, when the compounds of formula EP-II are O-deprotected, they can be cyclized to yield the compounds of EP-I.

SUMMARY OF THE INVENTION

This invention provides some new synthetically obtained 2-acyl-4,5,8,8a-tetrahydro-4-oxocyclopropan(c-)pyrrolo(3,2-e) indole derivative compounds of formula I' (see General Formulae Chart), as defined hereinafter, which are useful as uv light absorber substances, or as chemical intermediates and as prodrugs for known spirocyclopropylpyrroloindole CC-1065 analogs. Representative formula I' compounds have also been shown to possess useful ranges of antitumor activity in standard laboratory animal tests. Compounds of formula I', where X is halogen and Z is hydrogen, are useful as antibacterial compounds. The compounds of this invention are obtained by chemical processes shown in Chart A and detailed in the examples.

DETAILED DESCRIPTION OF THE INVENTION

More specifically, this invention provides new chemical compounds of general Formula I' (see GENERAL FORMULA sheet) wherein W is selected from $C_1$-$C_5$ alkyl, phenyl or hydrogen;

wherein X is selected from azido, a halogen atom, cyanate, thiocyanate, isocyanate, thioisocyanate, phosphate diester (—PO(OR)$_2$), phosphonyl (—O—PO$_2$R), thiophosphonyl (—O—PSOR), sulfinyl (—O—SOR) or sulfonyl (—O—SO$_2$R);

wherein Y is selected from hydrogen, —C(O)R, —C(S)R, —C(O)OR$_1$, —S(O)$_2$R$_1$, —C(O)NR$_2$R$_3$, —C(S)NR$_2$R$_3$, or —C(O)NHSO$_2$R$_4$; with the proviso that when X is a bromo, chloro or iodo atom, Y is not hydrogen;

wherein Z is selected from the group consisting of $C_1$-$C_5$ alkyl, phenyl or hydrogen;

wherein R is selected from the group consisting of $C_1$-$C_{20}$ alkyl; $C_2$-$C_6$ alkenyl; $C_2$-$C_6$ alkynyl; phenyl optionally substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro; naphthyl optionally substituted with one or 2 $C_1$-$C_4$ alkyl, $C_1$-$C_3$ alkoxy, halo, trifluromethyl, $C_2$-$C_6$dialkylamino, $C1$-$C_3$ alkylthio or nitro;

wherein $R_1$ is selected from $C_1$-$C_{20}$ alkyl or phenyl optionally substituted with one, 2 or 3 $Ci$—$C_4$ alkyl, $C_1$-$C_3$ alkoxy, halo, $C_1$-$C_3$alkylthio, trifluoromethyl, $C_2$-$C_6$ dialkylamino, or nitro;

wherein $R_2$ and $R_3$, being the same or different, are selected from hydrogen, $C_1$-$C_{20}$ alkyl, or phenyl optionally substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro; with the proviso that both $R_2$ and $R_3$ can not be phenyl or substituted phenyl;

wherein $R_4$ is selected from $C_1$-$C_{10}$ alkyl; phenyl optionally substituted with one, 2 or 3 $C_1$-$C_4$ alkyl, $C_1$-$C_3$ alkoxy, halo, $C_1$-$C_3$alkylthio, trifluoromethyl, $C_2$-$C_6$ dialkylamino, or nitro; naphthyl optionally substituted with one or 2 $C_1$-$C_4$ alkyl, $C_1$-$C_3$ alkoxy, halo, trifluromethyl, $C_2$-$C_6$ dialkylamino, $C_1$-$C_3$ alkylthio or nitro;

wherein $R_5$ is an acyl group selected from the group consisting of a compound of formula (i), (ii), (iii), (iv), (v), (vi), (vii), (viii), (ix), (x), (xi), (xii), (xiii), (xtv), (xv), (xvi), (xvii), (xviia), (xviib), (xviii), (xix), (xx), (xxi), (xxii) as defined in Chart C, and when any of $X_1$ to $X_6$ is OH or $NH_2$, then each of the $R_5$groups represented by (it), (vi), (viii), (ix), (x), (xvii), (xviia), (xviib), (xviii), (xix), (xx), (xxi)or (xxii)may be coupled with each other forming the dimer combinations set forth in Chart D, wherein the respective $R_5$ groups are bound together via an oxycarbonyl (—OOC—) or an amide (—NH-CO—) linkage.

Illustrative examples of the thus formed dimer are given in Chart E.

W is preferably methyl.

X is preferably halogen, more preferably chloro or bromo.

Y is preferably —COR, wherein R is selected from $C_1$-$C_{10}$ alkyl; phenyl optionally substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro; —C(O)NHSO$_2$R$_4$; or —C(O)NR$_2$R$_3$.

Z is preferably hydrogen.

$R_5$ is preferably the dimer combination viii+xviib bound together with the amide linkage.

An embodiment of this invention are the new compounds of general formula I' wherein Y is selected from hydrogen, —C(O)R,C(S)R,C(O)OR$_1$, —S(O)$_2$R$_1$, —C(O)NR$_2$R$_3$, —C(S)NR$_2$R$_3$, or —C(O)NHSO$_2$R$_4$; with the proviso that when X is a halogen atom, Y is not hydrogen.

Halogen atom (halo) refers to a bromo, chloro, iodo or fluoro atom.

Examples of $C_1$-$C_{20}$ alkyl are methyl, ethyl, propyl, butyl and the like, including isomeric forms thereof. Examples of $C_1$-$C_3$ alkoxy are methoxy, ethoxy, propoxy and isomeric forms thereof. Examples of $C_2$-$C_6$ dialkylamino are dimethylamino, diethylamino, methylethylamino, dipropylamino and ethylpropylamino. Examples of aminocarbonylalkyl(-$C_1$-$C_{10}$) are aminocarbonylpentyl (—NHCOC$_5$H$_{11}$) and aminocarbonylmethyl (—NHCOCH$_3$).

The compounds of formula I' on the GENERAL FORMULA sheet can be named as derivatives of the numbering system (B') shown on the GENERAL FORMULA sheet, Such compounds will contain the 1,2,3,6-tetrahydro-3-R$_5$-8-W-5-Y-benzo[1,2-b:4,3-b']dipyrrol-l-[Z-CH(X)]structure.

The compounds of Formula I' are drawn as the racemic mixture and include the natural isomer of Formula I'a which can be resolved from the racemic mixture and/or prepared from starting materials of the natural, i.e. 1(S)-configuration.

Examples of Formula I' compounds of this invention include:

(S)-N-[2-[[5-(acetyloxy)-1-(chloromethyl)-1,6-dihydro-8-methylbenzo[1,2-b:4,3-b']dipyrrol-3(2H)-yl]carbonyl]-1H-indol-5-yl-1H-indole-2-carboxamide (Cpd #1)

(S)-N-[2-[[5-(acetyloxy)-1-(chloromethyl)-1,6-dihydro-8-methylbenzo[1,2-b:4,3-b']dipyrrol-3(2H)-yl]carbonyl]-1H-indol-5-yl-2-benzofurancarboxamide (Cpd #2A)

(S)-6-[[5-[(2-benzofuranylcarbonyl)amino]-1H]indol-2-yl]carbonyl]-8-(chloromethyl)-3,6,7,8-tetrahydro-1-methylbenzo [1,2-b: 4,3-b']dipyrrol-4-yl hexanoate (Cpd #2B)

(S)-N-[2-[[5-(benzoyloxy)-1-(chloromethyl)-1,6-dihydro-8-methylbenzo[1,2-b:4,3-b']dipyrrol-3(2H)-yl]carbonyl]-1H-indol-5-yl]-2-benzofurancarboxamide (Cpd #2C)

(S)-6-[[5-[(2-benzofuranylcarbonyl )amino]-1H-indol-2-yl]carbonyl]-8-(chloromethyl)-3,6,7,8-tetrahydro-1-methylbenzo[1,2-b:4,3-b']dipyrrol-4-yl tetradecanoate (Cpd #2D)

(S)-6-[[5-[(2-benzofuranylcarbonyl )amino]-1H-indol-2-yl]carbonyl]-8-(chloromethyl)-3,6,7,8-tetrahydro-1-methylbenzo[1,2-b:4,3-b']dipyrrol-4-yl decanoate (Cpd #2E)

(S)-6-[[5-[(2-benzofuranylcarbonyl)amino]-1H-indol-2-yl]carbonyl]-8-(chloromethyl)-3,6,7,8-tetrahydro-1-methylbenzo[1,2-b:4,3-b']dipyrrol-4-yl dodecanoate (Cpd #2F)

(S)-N-[2-[[1-(azidomethyl)-1,6-dihydro-5-hydroxy-8-methylbenzo[1,2-b:4,3-b']dipyrrol-3(2H)-yl]carbonyl]-1H-indol-5-yl]-2-benzofurancarboxamide (Cpd #6)

(S)-N-[2-[[5-(benzoyloxy)-1-(bromomethyl)-1,6-dihydro-8-methylbenzo[1,2-b:4,3-b']dipyrrol-3(2H)-yl]carbonyl]-1H-indol-5-yl] 2-benzofurancarboxamide (Cpd #2G)

(S)-6-[[6-[[6-(aminocarbonyl)-3,6,7,8-tetrahydro-5-hydroxy-4-methoxybenzo[1,2-b:4,3-b']dipyrrol-2-yl]carbonyl]-3,6,7,8-tetrahydro-5-hydroxy-4-methoxybenzo[1,2-b:4,3-b']dipyrrol-2-yl]carbonyl]-8-(chloromethyl)-3,6,7,8-tetrahydro-1-methylbenzo[1,2-b:4,3-b']dipyrrol-4-yl decanoate (Cpd #3)

(S)-6-[[6-[(6-(aminocarbonyl)-3,6,7,8-tetrahydro-5-hydroxy-4-methoxybenzo[1,2-b: 4,3-b']dipyrrol-2-yl]carbonyl]-3,6,7,8-tetrahydro-5-hydroxy-4-methoxybenzo[1,2-b:4,3-b']dipyrrol-2-yl]carbonyl]-8-(chloromethyl)-3,6,7,8-tetrahydro-1-methylbenzo[1,2-b:4,3-b']dipyrrol-4-yl tetradecanoate (Cpd #4);

(S)-6-[[6-[[6-(aminocarbonyl)-3,6,7,8-tetrahydro-5-hydroxy-4-methoxybenzo[1,2-b:4,3-b']dipyrrol-2-yl]carbonyl]-3,6,7,8-tetrahydro-5-hydroxy-4-methoxybenzo[1,2-b:4,3-b']dipyrrol-2-yl]carbonyl]-8-(chloromethyl)-3,6,7,8-tetrahydro-1-methylbenzo[1,2-b:4,3-b']dipyrrol-4-yl hexanoate (Cpd #5)

butyl 1-ethyl-3,6,7,8-tetrahydro-6-[[5-[(2-quinolinylcarbonyl)amino]-1H-indol-2-yl]carbonyl]-8-(thiocyanatomethyl)benzo[1,2-b:4,3-b']dipyrrol-4-yl carbamate;

O-[8-(bromoethyl)-3,6,7,8-tetrahydro-6-[[5-[(2-quinoxalinylcarbonyl)amino]-2-benzofuranyl]carbonyl]benzo[1,2-b:4,3-b']dipyrrol-4-yl] O-phenyl thiocarbamate;

O-[8-ethyl-3,6,7,8-tetrahydro-1-methyl-6-[[6-methyl-1H-indol-2-yl)carbonyl ]amino]-2-quinolinyl]carbonyl]benzo[1,2-b:4,3-b']dipyrrol-4-yl] O-(1-methylethyl) thiocarbamate;

4-nitro-2-[[1-(azidomethyl)-1,6-dihydro-8-methyl-5-[(methylsulfonyl)oxy]benzo[1,2-b:4,3-b']dipyrrol-3 (2H)-yl]carbonyl]-1H-indol-5-yl 1H-pyrrole-2-carbamate;

5,6,-dimethyl-2-[[1-(fluoromethyl)-1,6-dihydro-5-[[(4-methylphenyl)sulfonyl]oxy]-8-propylbenzo[1,2-b: 4,3-b']dipyrrol-3 (2H)-yl]carbonyl]-6-quinoxalinyl 2-benzofurancarbamate;

O-6-[[5-[(2-benzofuranylcarbonyl)amino]-1H-indol-2-yl]carbonyl]-8-(chloromethyl)-3,6,7,8-tetrahydro-1-methylbenzo[1,2-b:4,3-b']dipyrrol-4-yl] butylthiocarbamate;

methylphenyl-O-[8-(bromomethyl)-3,6,7,8-tetrahydro-6-[[5-[(1H-indol-2-yl carbonyl)amino]-1H-benzimidazo]-2-yl]carbonyl]benzo1,2-b:4,3-b']dipyrrol-4-yl] thiocarbamate;

N-[2-[[1-(chloromethyl)-1,6-dihydro-8-methyl-5-[[(phenylamino)carbonyl]oxy]benzo[1,2-b:4,3-b']dipyrrol-3 (2H)-yl]carbonyl]-1H-indol] -5-yl]-2-benzofurancarboxamide;

[3-[[5-[[(6,7-dichloro-2-benzofuranyl)carbonyl]amino]-2-benzoazolyl]carbonyl]-1,2,3,6-tetrahydro-5-[[(phenylamino)carbonyl]oxy]benzo[1,2-b: 4,3-b']dipyrrol-1-yl]methyl cyanate;

N-[2-[[1-(chloromethyl)-1,6-dihydro-8-methyl-5-[[(methylamino)carbonyl]oxy]benzo[1,2-b:4,3-b']dipyrrol-3 (2H)-yl]carbonyl]-5-benzothiazolyl]-5-(trifluoromethyl)-2-benzoxazolecarboxamide;

(S)-N-[2-[[1-(chloromethyl)-1,6-dihydro-8-methyl-5-[[(phenyl amino) carbonyl]oxy]benzo[1,2-b:4,3-b']dipyrrol-3(2)-yl]carbonyl]-1H-indol-5-yl]-2-benzofurancarboxamide (Cpd #10A)

(S)-3-[[6-[(2-benzofuranylcarbonyl)amino]-1H-indol-2-yl]-carbonyl]-8-(chloromethyl)-3,6,7,8-tetrahydro-1-methylbenzo[1,2-b 4,3-b']dipyrrol-4-yl ester, butyl carbamic acid (Cpd #10B)

(S)-3-[[6-[(2-benzofuranylcarbonyl)amino]-1H-indol-2-yl]carbonyl]-8-(chloromethyl)-3,6,7,8-tetrahydro-1-methylbenzo[1,2-b 3,4-b']dipyrrol-4-yl ester, 2,2-dimethyl propanoic acid (Cpd #10C)

(S)-6-[[5-[(2-benzofuranylcarbonyl)amino]-1H-indol-2-yl]-carbonyl]-8-(chloromethyl)-3,6,7,8-tetrahydro-1-methylbenzo[1,2-b 4,3-b']dipyrrol-4-yl ester, [4-(trifluoromethyl)phenyl]-carbamic acid (Cpd #10D)

(S)-6-[[5-[(2-benzofuranylcarbonyl)amino]-1H-indol-2-yl]carbonyl]-8-(chloromethyl)-3,6,7,8-tetrahydro-2-methyl]benzo [1,2-b 4,3-b']dipyrrol-4-yl ester, (3,5-dimethylphenyl)-carbamic acid (Cpd 10E);

(S)-6-[[5-[(2-benzofuranylcarbonyl)amino]-1H-indol-2-yl]carbonyl]-8-(chloromethyl)-3,6,7,8-tetrahydro-1-methylbenzo[1,2-b 4,3-b']dipyrrol-4-yl ester, (4-chlorophenyl)-carbamic acid (Cpd #10F)

(S)-6-[[5-[(2-benzofuranylcarbonyl)amino]-1H-indol-2-yl]carbonyl]-8-(chloromethyl)-3,6,7,8-tetrahydro-1-methylbenzo[1,2-b 4,3-b']dipyrrol-4-yl ester, (3,4-difluorophenyl)-carbamic acid (Cpd 10G);

(S)-8-(chloromethyl)-6-[[5-[[[6-(diethylamino)-2-benzofuranyl]carbonyl]amino]-1H-indol-2-yl]carbonyl]-3,6,7,8-tetrahydro-1-methylbenzo[1,2-b 4,5-b']dipyrrol-4-yl ester, 2,2-dimethyl-propanoic acid (Cpd #11A)

(S)-N-[2-[[1-(chloromethyl)-1,6-dihydro-8-methyl-5-[[(phenylamino)carbonyl]oxy]benzo[1,2-b 4,3-b']dipyrrol-3(2H)-yl]carbonyl]-1H-indol- 5-yl]-6-(diethylamino)-2-benzofurancarboxamide (Cpd #11B).

The compounds of Formula I' are readily prepared by reacting the appropriate spirocyclopropylcyclohexadienyl analog (Formula I) with the Y-X reagent (Chart A) or with H-X and then acylating with Y-X' (Chart A') where X' is an active leaving group, for example halide, azide, sulfonate, and the like. The starting spirocyclopropyhyclohexadienyl analog (Formula I) is dissolved in an inert solvent such as methylene chloride, tetrahydrofuran (THF), N,N-dimethylformamide (DMF, DMFA), dimethylacetamide (DMA), pyridine, dioxane, N-methylpyrrolidone and the like. The resultant solution is treated with the reagent Y-X (where X and Y as defined above) and the solution stirred at ambient temperature until thin layer chromatography (TLC) shows the reaction to be complete (normally for reactive acyl halides in a few minutes but for weak acids or acylating agents a few hours or days may be required. For very reactive reagents the temperature may be lowered to −20° C. or less and for relatively unreactive addents the temperature may be raised to 80° C. or higher depending upon the solvent). When the reaction is complete, the solution is diluted with an appropriate solvent (methylene chloride, ethyl acetate, ether, THF (with brine), and the like. The organic layer is extracted with a mild base such as sodium or potassium bicarbonate, washed with water, dried by a suitable drying agent such as anhydrous magnesium sulfate or anhydrous sodium sulfate. Filtration of the drying agent and evaporation of the solvent leaves the desired product (Formula I') which may be used as such or purified by crystallization or chromatography by methods well know to those skilled in the art.

EXAMPLE 1

Preparation of (S)-N-[2-[[5-(acetyloxy)-1-(chloromethyl)-1,6-dihydro-8-methylbenzo [1,2-b: 4,3-b']dipyrrol-3(2H)-yl]carbonyl]-1H-indol-5-yl-1H-Indole-2-carboxamide; Cpd #1

15 mg (0.028 mmol) of (S)-N-[2-[[1-(chloromethyl)-1,6-dihydro-5-hydroxy-8-methylbenzo[1,2-b:4,3-b']dipyrrol-3(2H)-yl]carbonyl]-1H-indol-5-yl]-1H-Indole-2-carboxamide is dissolved in 2 ml of dry pyridine at 5° C., degassed with nitrogen and treated with 0.005 ml of acetyl chloride. After 30 min. at 5° C., the solution is warmed to room temperature, quenched with 1 ml of water, diluted with 50 ml of ethyl acetate, and washed with two 20 ml portions of 1:1 brine/1N hydrochloric acid, and then brine. The solution is dried with sodium sulfate, filtered, adsorbed on 1 g of Celite TM, and flash chromatographed on 10 g of silica gel, eluting with 50% ethyl acetate in hexane to give in fractions (25 ml) 6–12 the title compound as a solid.

NMR: (d6-acetone, $\delta$) 2.3(s,3H); 2.4(d,3H); 3.6–3.8 (m,1H); 3.9–4.3(m,2H); 4,6–5.0 (m,2H); 7.0–7.8 (m,9H); 8.1 (s,1H); 8.4 (s,1H); 9.7 (s,1H); 10.4 (s,1H); 11.0 (s,1H); 11.1 (s,1H).

M.S. (FAB) Calcd for $C_{32}H_{26}ClN_5O_4$: 579.1673; Found: 579.1662

UV:MeOH $\lambda$max 311; $\alpha$ 82; $\epsilon$ 47,800.

EXAMPLE 2

Reaction of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide with acid chlorides A 10 mg (0.02 mmol) quantity of (7bR)-N-[2-[(4,5,8,8a-tetrahydro-7-methyl-4-oxocyclopropa[c]pyrrolo[3,2-e]indol-2 (1H)-yl)carbonyl]-1H-indol-5-yl]-2-benzofurancarboxamide is dissolved in 150 $\mu$l pyridine. 2 equivalents of the acid chloride or bromide is added and the reaction mixture stirred for 5–30 minutes under nitrogen at room temperature. The reaction progress is checked by HPLC or TLC. When completed, one drop of water is added and everything evaporated under vacuum. The crude product is chromatographed over 100 to 1 silica gel, eluting with acetone-hexane. 0.5/1.0 ml fractions are collected and analyzed by TLC. The fractions containing product are combined and evaporated to yield the desired compound.

EXAMPLE 2A

Preparation of (S)-N-[2-[[5-(acetyloxy)-1-(chloromethyl)-1,6-dihydro-8-methylbenzo[1,2-b:4,3-b']dipyrrol-3(2H)-yl]carbonyl]-1H-indol-5-yl-2-benzofurancarboxamtde (Cpd #2A)

Following the general procedure of Example 2, 3 $\mu$l of acetyl chloride is added to a 10 mg (0.02 mmol) quantity of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide dissolved in 150 μl pyridine. The reaction is stirred for 5 min under nitrogen at room temperature. One drop of water is added and everything evaporated under vacuum. The crude product is chromatographed over 1 g silica gel, eluting with 20 ml acetone-hexane (40/60), 10 ml (50/50) and 10 ml (60/40); $R_f$ 0.71. The 0.5 ml fractions (13-28) containing the title compound are combined and evaporated. The crude product is purified on reverse phase C18 with methanol-water (80/20);

TLC (silica gel): $R_f$=0.71 in acetone-hexane (50/50).
NMR: (d6-acetone, δ) 2.344 (s,3H); 2.432 (d,3H); 3.62-3.75 (dd,1H); 3.91-4.04 (dd,1H); 4.12-4.29 (m,1H); 4.69-4.88 (m,2H); 7.145 (d,1H); 7.21 (s,1H); 7.30-7.71 (m,6H); 7.77-7.82 (dd,1H); 8.02 (s,1H); 8.36-8.40 (m,1H); 9.83 (s,1H).

EXAMPLE 2B

Preparation of
(S)-6-[[5-[(2-benzofuranylcarbonyl)amino]-1HI indol-2-yl]carbonyl]-8-(chloromethyl)-3,6,7,8-tetrahydro-1-methylbenzo[1,2-b:4,3-b']dipyrrol-4-yl hexanoate (Cpd #2B)

Following the general procedure of Example 2, 5 μl of hexanoyl chloride is added to a 10 mg (0.02 mmol) quantity of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide dissolved in 150 μl pyridine. The reaction Is stirred for 15 min under nitrogen at room temperature. One drop of water is added and everything evaporated under vacuum. The crude product is coated on 100 mg of silica gel, placed on a 1.5 g silica gel column and eluted with hexane-acetone (40/60). The 0.5ml fractions (9-15) containing the title compound are combined and evaporated to yield the title compound.

TLC (silica gel): $R_f$=0.76 in acetone-hexane (50/50).
NMR: (d6-acetone, δ) 0.89-1.02 (t,3H); 1.30-1.50 (d,6H); 1.71-1.88 (q,2H); 2.74 (t,2H); 3.66-3.80 (dd,1H); 3.97-4.08 (dd,1H); 4.20-4.34 (d,1H); 4.80-4.94 (m,2H); 7.19 (bs,1H); 7.25-7.29 (d,1H); 7.34-7.77 (d,6H); 7.81-7.89 (d,1H); 8.10 (s,1H); 8.45 (s,1H); 9.77 (s,1H); 10.27 (bs,1H); 10.95 (bs,1H).

EXAMPLE 2C

Preparation of
(S)-N-[2-[[5-(benzoyloxy)-1-(chloromethyl)-1,6-dihydro-8-methylbenzo[1,2-b:4,3-b']dipyrrol-3 (2H)-yl]carbonyl]-1H-indol-5-yl]-2-benzofurancarboxamide (Cpd #2C)

Following the general procedure of Example 2 6 μl of benzoyl chloride is added to a 11 mg (0.022 mmol) quantity of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide dissolved in 150 μl pyridine. The reaction is stirred for 10 min under nitrogen at room temperature. One drop of water is added and everything evaporated under vacuum. The crude product is coated on 100 mg of silica gel, placed on a 1.5 g silica gel column and eluted with hexane-acetone (40/60). The 0.5ml fractions (9-22) containing the title compound are combined and evaporated to yield the title compound.

TLC (silica gel): $R_f$=0.34 in acetone-hexane (40/60).
NMR: (d6-acetone, δ) 2.48 (s,3H); 3.68-3.83 (dd,1H); 3.97-4.10 (dd,1H); 4.20-4.36 (m,1H); 4.77-4.93 (m,2H); 7.17 (bs,1H); 7.24-7.29 (d,1H); 7.32-7.77 (m,9H); 7.78-7.86 (d,1H); 8.02-8.11 (m,1H); 8.20-8.32 (m,2H); 8.44 (s,1H); 9.66 (bs,1H); 10.52 (bs,1H); 10.97 (bs,1H).

EXAMPLE 2D

Preparation of
(S)-6-[[5-[(2-benzofuranylcarbonyl)amino]-1H-indol-2-yl]carbonyl]-8-<chloromethyl)-3,6,7,8-tetrahydro-1-methylbenzo[1,2-b:4,3-b']dipyrrol-4-yl tetradecanoate (Cpd #2D)

Following the general procedure of Example 2, 10 μl of myristoyl chloride is added to a 10 mg (0.02 mmol) quantity of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide dissolved in 150 μl pyridine. The reaction is stirred for 5 min under nitrogen at room temperature. One drop of water is added and everything evaporated under vacuum. The crude product is coated on 100 mg of silica gel, placed on a 1.5 g silica gel column and eluted with hexane-acetone (70/30). The 1 ml fractions (9-14) containing the title compound are combined and evaporated to yield the title compound.

TLG (silica gel): $R_f$=0.65 in acetone-hexane (30/70).
NMR: (d6-acetone, δ) 0.85-0.96 (t,3H); 1.24-1.54 (m20H); 1.72-1.88 (q,2H); 2.47 (s,3H); 2.68-2.80 (t,2H); 3.64-3.80 (dd,1H); 3.96-4.08 (dd,1H); 4.20-4.32 (m,1H); 4.76-4.94 (m,2H); 7.12 (s,1H); 7.27 (s,1H); 7.35-7.77 (m,6H); 7.80-7.88 (d,1H); 8.10 (s,1H); 8.47 (s,1H); 9.70 (s,1H); 10.25 (bs,1H); 10.99 (bs,1H).

EXAMPLE 2E

Preparation of
(S)-6-[[5-[(2-benzofuranylcarbonyl)amino]-1H-indol-2-yl]carbonyl]-8-(chloromethyl)-3,6,7,8-tetrahydro-1-methylbenzo[1,2-b:4,3-b']dipyrrol-4-yl decanoate (Cpd #2E)

Following the general procedure of Example 2, 9 μl of decanoyl chloride is added to a 10 mg (0.02 mmol) quantity of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide dissolved in 150 yl pyridine. The reaction is stirred for 30 min under nitrogen at room temperature. One drop of water is added and everything evaporated under vacuum. The crude product is coated on 100 mg of silica gel, placed on a 1.2 g silica gel column and eluted with hexane-acetone (60/40). The 1 ml fractions (8-16) containing the title compound are combined and evaporated to yield the title compound. The more polar chlorophenol is eluted with hexane-acetone (50/50), fractions collected and evaporated, added to 100 μl pyridine and 5 μl decanoyl chloride for 30 min. Worked up as above. The product in fractions (5-13) is combined with the initial crop (fractions 8-16) to yield a total of 8 mg. of title compound.

TLC (silica gel): $R_f$=0.69 in acetone-hexane (40/60).
NMR: (d6-acetone, δ) 0.84-0.98 (t,3H); 1.25-1.53 (m,12H); 1.72-1.88 (q,2H); 2.484 (d,3H); 2.67-2.80 (t,2H); 3.66-3.80 (dd,1H); 3.97-4.10 (dd,1H); 4.20-4.33 (m,1H); 4.76-4.94 (m,2H); 7.16 (s,1H); 7.27 (s,1H); 7.34-7.77 (m,6H); 7.81-7.88 (d,1H); 8.09 (s,1H); 8.44 (d,1H); 9.75 (s,1H); 10.27 (bs,1H); 10.85 (bs,1H).

EXAMPLE 2F

Preparation of (S)-6-[[5-[(2-benzofuranylcarbonyl)amino]-1H-indol-2-yl]carbonyl]-8-(chloromethyl)-

3,6,7,8-tetrahydro-1-methylbenzo[1,2-b:4,3-b']dipyrrol-4-yl dodecanoate (Cpd #2F);

Following the general procedure of Example 2, 10 μl of lauroyl chloride is added to a 10 mg (0.02 mmol) quantity of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide dissolved in 150 μl pyridine. The reaction is stirred for 5 min under nitrogen at room temperature. The reaction mixture is diluted with acetone and evaporated under vacuum. The crude product is coated on 150 mg of silica gel, placed on a 1.5 g silica gel column and eluted with hexane-acetone, (70/30). The 1 ml fractions (6-9) containing the title compound are combined and evaporated to yield the title compound.

TLC (silica gel): $R_f = 0.70$ in acetone-hexane (40/60).
NMR: (d6-acetone, δ) 0.84–0.97 (t,2H); 1.24–1.53 (m,16H); 1.72–1.89 (q,2H); 2.475 (d,3H); 2.68–2.80 (t,2H); 3.66–3.80 (dd,1H); 3.96–4.08 (dd,1H); 4.18–4.33 (m,1H); 4.74–4.94 (m,2H); 7.16 (s,1H); 7.27 (s,1H); 7.35–7.76 (m,6H); 7.82–7.88 (dd,1H); 8.10 (s,1H); 8.45 (d, 1H); 9.73 (s, 1H); 10.26 (bs, 1H); 10.95 (bs, 1H).

EXAMPLE 2G

Preparation of (S)-N-[2-[[5 (benzoyloxy) 1 (bromomethyl)-1,6-dihydro-8-methylbenzo[1,2-b:4,3-b']dipyrrol-3 (2H)-yl]carbonyl]-1H-indol-5-yl] 2-benzofurancarboxamide (Cpd #2G)

Following the general procedure of Example 2, 5 μl of benzoyl bromide is added to a 10 mg (0.02 mmol) quantity of (7bR)-N-[2-[(4,5,8,8a-tetrahydro-7-methyl-4-oxocyclopropa[c]pyrrolo[3,2-e]indol-2(1H)-yl)carbonyl]-1H-indol-5-yl]-2-benzofurancarboxamide dissolved in 150 μl pyridine. The reaction is stirred for 15 min under nitrogen at room temperature. One drop of water is added and everything evaporated under vacuum. The crude product is coated on 150 mg of silica gel, placed on a 1.3 g silica gel column (80/20 hexane-acetone) and eluted with a gradient of hexane-acetone (80/20 to 40/60). The 0.5 ml fractions (25–30) containing the title compound are combined and evaporated to yield the title compound.

TLC (silica gel): $R_f = 0.55$ in acetone-hexane (50/50).
NMR: (d6-acetone, δ) 2.483 (s,3H); 3.57–3.72 (t,1H); 3.88–3.99 (dd,1H); 4.23–4.42 (m,1H); 4.76–4.93 (m,2H); 7.17 (s,1H); 7.24 (s.1H); 7.32–7.78 (m,9H); 7.78–7.87 (d,1H); 8.17–8.32 (m,3H); 8.43 (s,1H); 9.67 (s,1H); 10.53 (bs,1H); 10.95 (bs,1H).

EXAMPLE 3

Preparation of (S)-6-[[6-[[6-(aminocarbonyl)-3 6 7,8-tetrahydro-5-hydroxy-4-methoxybenzo[1,2-b:4,3-b']dipyrrol-2-yl]-carbonyl]-3,6,7,8-tetrahydro-5-hydroxy-4-methoxybenzo[1,2-b:4,3-b']dipyrrol-2-yl]carbonyl]-8-(chloromethyl)-3,6,7,8-tetrahydro-1-methylbenzol1,2-b:4 3-b']dipyrrol-4-yl decanoate (Cpd #3)

CC-1065 (10 4 mg 0 015 mM) is dissolved in pyridine (150 μl) and put under an atmosphere of nitrogen. Decanoyl chloride (10 μl) is added, and the reaction is stirred at room temperature for 50 minutes. The crude solid product is obtained by precipitation with water and centrifugation. It is purified by column chromatography on 2 g of silica gel in (14–86) dimethylformamide toluene. Fractions are of one or two ml. The desired product, found in fractions 7–15, weight 7.1 mg (54% yield).

TLC (silica gel): $R_f = 0.54$ in DMF-toluene (14/86).

MS(FAB): Calcd. for $C_{47}H_{52}ClN_7O_9$: 893.3515. Measured: 893.3472.

EXAMPLE 4

Preparation of (S)-6-[[6-[[6-(aminocarbonyl)-3,6,7,8-tetrahydro-8-hydroxy-4-methoxybenzo[1,2-b:4,3-b']dipyrrol-2-yl]-carbonyl]-3,6,7,8-tetrahydro-5-hydroxy-4-methoxybenzo[1,2-b:4,3-b']dipyrrol-2-yl]carbonyl]-8-(chloromethyl)-3,6,7,8-tetrahydro-1-methylbenzo[1,2-b:4,3-b']dipyrrol-4-yl myristoate (Cpd #4)

A 9.9 mg (0.014 mM) quantity of CC-1065 in dry pyridine (150 μl) under nitrogen is treated with myristoyl chloride (9 mg, 0.036 mM). After stirring three hours at room temperature the product is precipitated with water, and isolated by centrifugation. The solid (16 mg) is chromatographed on a 2.5 g silica gel column. Fractions of 1-2 ml are collected. Elution with (13–87) and (25–75) DMF toluene brought the product off in fractions 11-19. An 11% yield (1.5 mg) is obtained.

TLC (silica gel): $R_f = 0.63$ in DMF-toluene (13/87).
MS(FAB): Calcd. for $C_{51}H_{61}ClN_7O_9$: 950.4219. Measured: 950.4175.

EXAMPLE 5

Preparation of (S)-6-[[6-[[6-(aminocarbonyl)-3,6,7,8-tetrahydro-5-hydroxy-4-methoxybenzo[1,2-b:4,3-b']dipyrrol-2-yl]-carbonyl]-3,6,7,8-tetrahydro-5-hydroxy-4-methoxybenzo[1,2-b:4,3-b']dipyrrol-2-yl]carbonyl]-8-(chloromethyl)-3,6,7,8-tetrahydro-1-methylbenzo[1,2-b:4,3-b']dipyrrol-4-yl hexanoate (Cpd #5)

An 11 mg (0.016 mmole) quantity CC-1065 is dissolved in 150 μl pyridine. Add 4 μl hexanoyl chloride and follow the reaction by HPLC. Two more 4 μl portions of hexanoyl chloride are added after 35 and 70 minutes reaction time. (The reaction to the intermediate chlorophenol is fast but acylation to the desired hexanoate is not only slow but also not entirely selective since an even less polar product appears before all the chlorophenol has been converted to the desired hexanoate.) After a total of 3 hours reaction, the mixture is transferred to a conical test tube, and washed with 100 μl pyridine. Then 5 ml water is added and a solid precipitates. The solid is spun down in a centrifuge and the liquid phase removed. This procedure is repeated with 5 ml water and 1.5 ml methanol. The solid is then dried under vacuum. HPLC of the 3 washes shows only small amounts of material present as a mixture of product and less polar side product.

The solid residue is chromatographed over 2 g of silica gel 60 eluted with (20–80) acetone-methylene chloride. Two ml fractions are collected. Impure product is found in fractions 5–9. This material is rechromatographed over silica gel 60, this time eluting with 15 ml of (10–90) DMF-toluene and ad lib with (15–85) DMF-toluene. Two ml fractions are collected. The product is found by TIC in fractions 21–25.

TLC (Silica Gel GF): $R_f = 0.50$ in (20–80) acetone-methylene chloride; $R_f = 0.33$ in (15–85) DMF-toluene.

EXAMPLE 6

Preparation of (S)-N-[2-[[1-(azidomethyl)-1,6-dihydro-5-hydroxy-8-methylbenzo[1,2-b:4,3-b']dipyrrol-3 (2H)-yl]carbonyl]-1H-indol- 5-yl]-2-benzofurancarboxamide; (Cpd #6) from (7bR)-N-[2-[(4,5,-8,8a-tetrahydro-7-methyl-4-oxocyclopropa[c]pyrrolo[3,2-e]indol- 2(1H)-yl]carbonyl]-1H-indol-5-yl]-2-benzofurancarboxamide (73975)

A solution of hydrogen azide is prepared by treating a mixture of sodium azide (1.0 g, 15 mM), water (1 ml), and methylene chloride (7 ml) at 0 C with concentrated sulfuric acid (0.42 ml, 8 mM). After approximately 20 minutes, the methylene chloride solution is decanted from the solids. The solution is dried over anhydrous sodium sulfate and treated with 1,1,3,3-tetramethylguanidine (71 mg, 0.62 mM) to give a salt-acid mixture.

A 9.9 $m_E$ quantity (0.02 mM) of (7bR)-N-[2-[(4,5,8,8a-tetrahydro-7-methyl-4-oxocyclopropa[c]pyrrolo[3,2-e]indol-2 (1H)-yl]carbonyl]-1H-indol-5-yl]-2-benzofurancarboxamide (U-73975) is treated with 0.5 ml of the hydrogen azide solution. After stirring in the dark at room temperature for 1.5 hours, the reaction is evaporated under a nitrogen stream. The residue is purified on a 2.5 g reversed phase $C_{18}$ column. Eluents are (65–35) through (76–24) DMF-water. Fractions of 3–4 ml are collected. The product is found in fractions 17–19. It is crystallized from acetone-hexane. A 41% yield of crystals (4.5 mg) is obtained, while the mother liquors contained 4 mg of crude material. Both the crystalline product and mother liquors are re-chromatographed, each on 0.8 g of silica gel, in (40–60) acetonehexane. The desired product is slowly crystallized from acetonehexane. A 2.2 mg quantity of the pure azide analog is obtained.

MS (FAB), before re-purification: Calcd. for $C_{30}H_{23}N_7O_4$: 545.1811. Measured: 545.1795.

TLC (silica gel GF): $R_f$=0.26 in (40–60) acetone-hexane, R%f of chlorophenol=0.22 in same.

The O,N-bisacylated compounds of Formula I' can also be prepared in a single step as illustrated in Chart A" and Examples 7 and 8.

EXAMPLE 7

Preparation of
(S)-6-hexanoyl-8-chloromethyl-3,6,7,8-tetrahydro-1-methylbenzo[1,2-b:4,3-b']dipyrrol-4-yl hexanoate;
O,N-bis(hexanoyl)CPI A solution of 0.5 mg (0.002 mM) of CPI and 4-dimethylaminopyridine (one crystal) in dry pyridine is cooled to −78° under argon. Hexanoyl chloride (1 μl, 0.007 mM) is added and the reaction is maintained at 0° C. for two days. A similar reaction with CPI in acetone with $K_2CO_3$ as the base gives the same product. The products are diluted with methylene chloride, combined, and washed with water and 5% sodium bicarbonate solution. The aqueous layers are reextracted. Drying and concentration of the combined organic solutions give 6.5 mg of crude product. It is purified by preparative thin layer chromatography on a 5×17 cm. Analtech analytical plate, with (40–60–0.2) acetone-skellysolve B-triethylamine as the eluant. The desired product band is visualized by uv light, scraped off the plate into a scintered glass funnel, and eluted with (50–50) acetone-methylene chloride. Solvent evaporation leaves the product, (S)-6-hexanoyl-8-chloromethyl-3,6,7,8-tetrahydro-1-methylbenzo1,2-b:4,3-b']dipyrrol-4-yl hexanoate.

NMR (CDCl$_3$, TMS): 60.77–0.893 (M,6H); 1.26–1.38, (M,5H); 1.66–1.75 (m,4H); 2.20–2.40 (m, 1H); 2.34 (d, 3H); 2.44–2.50 (m,1H); 2.53–2.56 (t,2H); 3.32 (t,1H); 3.74–3.77 (m,1H); 3.89–3.92 (m, 1H); 4.06–4.10 (m,1H); 4.23(dd,1H); 6.91(s); 7.80(s); 8.01(s).

EXAMPLE 8

Preparation of
(S)-6-(4-chlorobenzoyl)-8-chloromethyl-3,6,7,8-tetrahydro-1-methylbenzo[1,2-b:4,3-b']dipyrrol-4-yl
4-chlorobenzoate To a 11.2 mg (0.056 mmol) of natural CPI is added 19.2 ml of 7.2 millimolar triethylamine in methylene chloride (0.138 mmol) and 17 ml of 7.9 millimolar chlorobenzoyl chloride in methylene chloride (0.134 mmol). After 1.5 hr stirring at room temperature in subdued light, TLC densitometry (Whatman LKC$_{18}$D) indicates the absence of CPI and the presence of a clean lipophilic component at Rf 0.3 (acetone-water 3:1). After overnight storage in the freezer, the solution is evaporated to dryness and the residue triturated with 3 ml of 85% methanol (aqueous). The suspension is briefly chilled and the solid collected, washed with 5 ml of 85% methanol in portions, and dried affording 30.7 mg of homogeneous diacylated product, TLC densitometry R$_f$0.31 on C18 with 3:1 acetone-water monitored by 250 nm UV light.

UV: $\lambda^{doxane}_{max}$ nm (ε) end abs., 243 (51,550) 271 (sh 21,750), 307 (sh 11,750) CD in dioxane: nm (molar ellipticity) 300 (−9,000), 250 (+18,000) 228 (−43,000) FAB-MS: m/z 513 (M+H)$_+$.

EXAMPLE 9

Preparation of
(S)-N-[2-[[5-phenylaminocarbonyloxy)-1-(chloromethyl)-1,6-dihydro-8-methylbenzo[1,2-b:4,3-b']dipyrrol-3 (2H)-yl]carbonyl]-1H-indol-5-yl-2-benzofurancarboxamide. (Cpd 10A)

A 10 mg (0.019 mM) quantity of (S)-N-[2-[[5-hydroxy-1-(chloromethyl)-1,6-dihydro-8-methylbenzo1,2-b: 4,3-b']dipyrrol-3(2H)-yl] carbonyl]-1H-indol-5-yl-2-benzofurancarboxamide is dissolved in freshly distilled THF and the solution stirred under nitrogen at 25° C. To the solution is added 2 microL (0.019 mM) of phenylisocyanate (PIC) and 0.5 microL of triethylamine (TEA). After stirring 18 hrs. the reaction is treated with an additional 1 microL of PIC. The reaction is then stirred another 72 hrs, at which time 0.5 microL more of TEA is added. After another 18 hrs. the reaction mixture is added to 200 mg of silica gel and evaporated under vacuum. The residue is placed on the top of 2 g of silica gel and eluted with acetone-hexane (30/70) followed by acetone-hexane (50/50). The fractions containing product, as found by TLC, are combined and concentrated giving the title compound.

TLC (silica gel): R$_f$=0.51 in acetone-hexane (40/60).

Mass Spectrum (FAB): 658, 539, 303, 237, 236, 187, 145.

The urethane-hydrochloride analogs can be prepared by reacting the appropriate chlorophenol analog (Formula II) with the appropriate isocyanate (Chart A'''). The starting chlorophenol analog (Formula II) is dissolved in the dark in an aprotic solvent(s) such as methylene chloride, tetrahydrofuran (THF), dioxane, toluene or combination thereof. To the resultant solution is added the appropriate isocyanate and a tertiary amine base such a as triethylamine, diisopropylethylamine or pyridine, and the like. The reaction mixture is stirred at ambient temperature until thin layer chromatography (TLC) shows the reaction to be complete (normally for reactive isocyanates in a few minutes but for weak agents a few hours or days may be required. For very reactive reagents the temperature may be lowered to −20° C. or less and for relatively unreactive addents the temperature may be raised to 80° C. or higher depending upon the solvent). When the reaction is complete, the reaction mixture is evaporated and the residue chromatographed over silica gel, eluting, for example with increasing concentrations of acetone in n-hexane. Fractions containing the desired product are identified by TLC, combined and evaporated to give the urethane analog.

EXAMPLE 10

Reaction of (S)-N-[2-[[1-chloromethyl)-1,6-dihydro-5-hydroxy-8-methylbenzo[1,2-b:4,3-b']dipyrrol-3(2H)-yl]-carbonyl]-1H-indole-5-yl]-2-benzofurancarboxamide with isocyanates A 0.015 mmol quantity of (S)-N-[2-[[21-chloromethyl)-1,6-dihydro-5-hydroxy-8-methylbenzo1,2-b:4,3-b']dipyrrol-3(2H)-yl]carbonyl]-1H-indole- 5-yl]-2-benzofurancarboxamide is dissolved in the dark in 1.0 ml of freshly distilled THF. Six equivalents of the isocyanate and 2 equivalents triethylamine (NEt$_3$) is added and the reaction mixture stirred from 1 hour to 30 days under nitrogen in the dark at room temperature. The reaction progress is checked by HPLC or TLC. When completed, the crude product is chromatographed over 100 to 1 silica gel, eluting with acetone-hexane. 0.5/1.0 ml fractions are collected and analyzed by TLC. The fractions containing product are combined and evaporated to yield the desired compound.

EXAMPLE 10A

Preparation of (S)-N-[2-[[1-(chloromethyl)-1,6-dihydro-8-methyl-5-[[(phenylamino)carbonyl]oxy]benzo[1,2-b:4,3-b']dipyrrol-3(2)-yl]carbonyl]-1H-indol-5-yl]-2-benzofurancarboxamide (Cpd #10A)

Following the general procedure of Example 10, 16 mg (0.14 mmol) of phenyl isocyanate and 4 mg (0.036 mmol) triethylamine is added to a 10 mg (0.019 mmol) quantity of (S)-N-[2-[[1-chloromethyl)-1,6-dihydro-5-hydroxy-8-methylbenzo[1,2-b:4,3-b']dipyrrol-3(2H)-yl]-carbonyl]-1H-indole-5-yl]-2-benzofurancarboxamide dissolved in the dark in 0.5 ml of THF. The reaction is stirred in the dark for 41 days under nitrogen at room temperature. The crude product is chromatographed over 2 g silica gel, eluting with acetone-hexane (30/70 and 50/50). The fractions containing the title compound are combined and evaporated.

TLC (silica gel): 40% acetone—60% hexane; Rf 0.50.
NMR: acetone: 2.45 (s, 3H); 3.63–3.77 (dd, 1H); 3.93–4.05 (dd, 1H); 4.15–4.30 (t, 1H); 4.68–4.90 (m, 2H); 7.00–7.12 (t, 1H); 7.17 (s, 1H); 7.22 (s, 1H); 7.28–7.41 (m, 3H); 7.43–7.50 (dd, 1H); 7.50–7.56 (dd 1H); 7.56–7.70 (m, 5H); 7.76–7.84 (dd, 1H); 8.13 (s, 1H); 8.37 (d, 1H); 9.41 (bs, 1H); 9.81 (bs, 1H); 10.5 (bs, 1H); 10.96 (bs, 1H);
MS: [N═H]+ at 658,660.
Fragment ions at 539, 303, 237, 236, 187 and 145.

EXAMPLE 10B

Preparation of (S)-3-[[6-[(2-benzofuranylcarbonyl)amino]-1H-indol-2-yl]carbonyl]-8-(chloromethyl)-3,6,7,8-tetrahydro-1-methylbenzo[1,2-b 4,3-b']dipyrrol-4-yl ester, butyl carbamic acid (Cpd #10B)

Following the general procedure of Example 10, 11 mg 0(0.11 mmol) of butyl isocyanate and 3 mg (0.029 mmol) NEt$_3$ is added to a 20 mg (0.038 mmol) quantity of (S)-N-[2-[[1-chloromethyl)-1,6-dihydro-5-hydroxy-8-methylbenzo[1,2-b:4,3-b']dipyrrol-3(2H)-yl]carbonyl]-1H-indole-5-yl]-2-benzofurancarboxamide dissolved in the dark in 1 ml of THF. The reaction is stirred tn the dark for 11 days under nitrogen at room temperature. The crude product is chromatographed over 3 g silica gel, eluting with acetone-hexane (40/60). The fractions containing the title compound are combined and evaporated. The product is further purified on 4 g silica gel, eluting with 30% ethyl acetate (EtOAc)—70% toluene.

TLC (silica gel): 30% EtOAc—70% toluene; Rf 0.38.

NMR: Acetone, TMS. 0.89 (t, 3H); 1.4–1.55 (m, 2H); 1.55–1.70 (m, 2H); 2.29 (s, 3H); 3.43 (6S, 2H); 3.59 (t, 1H); 3.85–4.0 (m, 1H); 4.10–4.25 (m, 1H); 4.65–4.90 (m, 2H); 7.20 (s, 1H); 7.36 (t, 1H); 7.4–7.7 (m, 6H); 7.78 (d, 1H); 7.97 (s, 1H); 8.64 (6s, 1H); 9.35 (6s, 1H); 10.11 (6s, 1H); 11.22 (6s, 1H).
MS: [M═H]+ at 638.640.
Fragment ions at 539, 538, 489, 303, 236, 235, 199, 187 and 145.

EXAMPLE 10C

Preparation of (S)-3-[[6-[(2-benzofuranylcarbonyl)amino]-1H-indol-2-yl]carbonyl]-8-(chloromethyl)-3,6,7,8-tetrahydro-1-methylbenzo[1,2-b 3,4-b']dipyrrol-4-yl ester, 2,2-dimethyl propanoic acid (Cpd #10C)

A 15 mg (0.03 mmol) quantity of (7bR)-N-[2-[[4,5,8,8a-tetrahydro-7-methyl-4-oxocyclopropa[c]pyrrolo[3,2-e]indol-2 (1H)-yl]carbonyl]-1H-indol-5-yl]-2-benzofurancarboxamide is dissolved at 25° C. in 200 microL of dry pyridine and the solution treated with 8 microL of pivaloyl chloride. After 30 min the reaction is treated with 1 drop of water and evaporated under vacuum. The residue is coated on 250 mg of silica gel and placed on top of a 2.5 g silica gel column. The column is eluted with acetone-hexane (40/60). The 1.5 mL fractions (8–12) containing the title compound are combined and evaporated to yield 10 mg of the title compound.

TLC (silica gel): 50% acetone—60% hexane; Rf 0.45.
NMR: Acetone, TMS.
1.43 (s, 9H); 2.45 (s, 3H); 3.66–3.77 (dd, 1H); 3.95–4.04 (dd, 1H); 4.18–4.30 (t, 1H); 4.73–4.90 (m, 2H); 7.11 (s, 1H); 7.22 (s, 1H); 7.32–7.40 (t, 1H); 7.45–7.53 (t, 1H); 7.55–7.71 (m, 4H); 7.78–7.83 (d, 1H); 8.04 (s, 1H); 4.40 (s, 1H); 9.75 (s, 1H); 9.99 (s, 1H); 10.90 (s, 1H).
MS: [M-H]+ at 623, 625; [M]+ at 622, 624. Measured: 623.2047, theory for $C_{35}H_{32}ClN_4O_5$: 623.2061.
Other fragment ions: 539, 320, 303, 237, 236, 199, 187, 145 and 57.

EXAMPLE 10D

Preparation of
(S)-6-[[5-[(2-benzofuranylcarbonyl)amino]-1H-indol-2-yl]carbonyl]-8-(chloromethyl)-3,6,7,8-tetrahydro-1-methylbenzo[1,2-b 4,3-b']dipyrrol-4-yl ester,
[4-(trifluoromethyl)phenyl]-carbamic acid (Cpd #10D)

Following the general procedure of Example 10, 40 mg (0.21 mmol) of 4-trifluoromethylphenyl isocyanate and 7 mg (0.072 mmol) triethylamine is added to a 20 mg (0.038 mmol) quantity of (S)-N-[2-[[1-chloromethyl)-1,6-dihydro-5-hydroxy-8-methylbenzo1,2-b:4,3-b']dipyrrol-3 (2H)-yl]carbonyl]-1H-indole-5-yl]-2-benzofurancarboxamide dissolved in the dark in 1 ml of THF. The reaction is stirred in the dark for 6 days under nitrogen at room temperature. The crude product is chromatographed over 2 g silica gel, eluting with acetonehexane (40/60). The fractions containing the title compound are combined and evaporated.

TLC (silica gel): 40% acetone-60% hexane; Rf 0.43.
NMR: Acetone, TMS.
2.47 (s, 3H); 3.67.3.77 (dd, 1H);3.97–4.05 (dd, 1H); 4.20–4.30 (t, 1H); 4,73–4.89 (m, 2H); 7.18 (s, 1H); 7.23 (s, 1H); 7.30–7.39 (t, 1H);7.44–7.52 (t, 1H); 7.54–7.73 (m, 6H); 7.76-7.90 (1m, 3H); 8.14 (s, 1H); 8.39 (d, 1H); 9.75 (s, 2H); 10.48 (s, 1H); 10.92 (s, 1H).
MS: [M=H]+ at 726,728; measured: 726.1748; theory for $C_{38}H_{28}ClF_3N_5O_5$: 726.1731. Other fragment ions: 725, 539, 538, 424, 303, 237, 236, 235, 199, 187, 145.

EXAMPLE 10E

Preparation of
(S)-6-[[5-[(2-benzofuranylcarbonyl)amino]-1H-indol-2-yl]carbonyl]-8-(chloromethyl)-3,6,7,8-tetrahydro-2-methyl]benzo [1,2-b 4,3-b']dipyrrol-4-yl ester,
(3,5-dimethylphenyl)carbamic acid (Cpd #10E)

Following the general procedure of Example 10, 35 mg (0.24 mmol) of 3,5-dimethylphenyl isocyanate and 7 mg (0.072 mmol) triethylamine is added to a 20 mg (0.038 mmol) quantity of (S)-N-[2-[[1-chloromethyl)-1,6-dihydro-5-hydroxy-8-methylbenzo[1,2-b:4,3-b']dipyrrol-3(2H)-yl]carbonyl]-1H-indole-5-yl]-2-benzofurancarboxamide dissolved in the dark in 1 ml of THF. The reaction is stirred in the dark for 7 days under nitrogen at room temperature. The crude product is chromatographed over 2 g silica gel, eluting with acetone-hexane (40/60). The fractions containing the title compound are combined and evaporated. Reparified over silica gel eluting with 10% DMF-90% toluene and again using 8% DMF—92% toluene.

TLC (silica gel): 40% acetone—60% hexane; Rf 0.49.
NMR: Acetone, TMS.
2.23 (s, 2H); 2.42 (s, 1H); 3.62–3.71 (dd, 1H); 3.93–4.01 (dd, 1H); 4.13–4.23 (t, 1H); 4.65–4.84 (m, 2H); 6.69 (s, 1H); 7.09 (s, 1H); 7.19 (s, 1H); 7.30–7.38 (t, 1H); 7.43–7.51 (t, 1H); 7.54–7.66 (m, 1H); 7.75–7.80 (d, 1H); 8.16 (s, 1H); 8.40 (s, 1H); 9.13 (s, 1H); 9.66 (s, 1H); 10.44 (s, 1H); 11.00 (s, 1H).
MS: [M=H]+ at 686,688; measured: 686.2173; theory for $C_{39}H_{33}ClN_5O_5$: 686.2170. Other fragment ions: 685, 539, 538, 384, 303, 237, 236, 199, 187, 145.

EXAMPLE 10F

Preparation of (S)-6-[[5-[(2-benzofuranylcarbonyl)amino]-1H-indol-2-yl]carbonyl]-8-(chloromethyl)-3,6,7,8-tetrahydro-1-methylbenzo[1,2-b 4,3-b']dipyrrol-4-yl ester, (4-chlorophenyl)carbamic acid (Cpd #10F)

Following the general procedure of Example 10, 35 mg (0.23 mmol) of 4-chlorophenyl isocyanate and 7 mg (0.072 mmol) triethylamine is added to a 20 mg (0.038 mmol) quantity of (S)-N-[2-[[1-chloromethyl)1,6-dihydro-5-hydroxy-8-methylbenzo[1,2-b:4,3-b']dipyrrol-3 (2H)-yl]carbonyl]-1H-indole-5-yl]-2-benzofurancarboxamide dissolved in the dark in 1 ml of THF. The reaction is stirred in the dark for 8 days under nitrogen at room temperature. The crude product is chromatographed over 2 g silica gel, eluting with acetone-hexane (40/60). The fractions containing the title compound are combined and evaporated. Rechromatographed over silica gel eluting with 5% DMF—95% toluene.

TLC (silica gel): 40% acetone—60% hexane; Rf 0.51.
NMR: Ace tone, TMS.
2.47 (s, 3H); 3.65–3.78 (t, 1H); 3.95–4.05 (d, 1H); 4.20–4.30 (t, 1H); 4.71–4.94 (m, 2H); 7.18 (s, 1H); 7.24 (s, 1H); 7.30–7.40 (m, 3H); 7.43–7.53 (t, 1H); 7.53–7.61 (m, 5H); 7.75–7.84 (d, 1H); 7.96 (s, 1H); 8.12 (s, 1H); 8.40 (s, 1H); 9.48 (s, 1H); 9.75 <s, 1H); 10.46 (s, 1H); 10.92 (s, 1H).
MS: [M=H]+ at 692,694. Measured: 692.1469; theory for $C_{37}H_{28}Cl_2N_5O_5$: 692. 1467.

EXAMPLE 10G

Preparation of (S)-6-[[5-[(2-benzofuranylcarbonyl)amino]-1H-indol-2-yl]carbonyl]-8-(chloromethyl)-3,6,7,8-tetrahydro-1-methylbenzo[1,2-b 4,3-b']dipyrrol-4-yl ester, (3,4-difluorophenyl)carbamic acid (Cpd #10G)

Following the general procedure of Example 10, 35 mg (0.23 mmol) of 3,4-difluorophenyl isocyanate and 7 $m_E$(0.072 mmol) triethylamine is added to a 20 mg (0.38 mmol) quantity of (S)-N-[2-[[1-chloromethyl)-1,6-dihydro-5-hydroxy-8-methylbenzo1,2-b:4,3-b']dipyrrol-3(2H)-yl]carbonyl]-1H-indole-5-yl]-2-benzofurancarboxamide dissolved in the dark in 1 ml of THF. The reaction is stirred in the dark for 10 days under nitrogen at room temperature. The crude product is chromatographed over 2 g silica gel, eluting with DMF-toluene (5/95). The fractions containing the title compound are combined and evaporated. TLC (silica gel): 40% acetone—60% hexane; Rf 0.55.
NMR: Ace tone, TMS.
2.45 (s, 3H); 3.62–3.75 (t, 1H); 3.90–4.03 (d, 1H); 4.15–4.28 (t, 1H); 4.67–4.86 (m, 2H); 7.14 (s, 1H); 7.22 (s, 1H); 7.23–7.41 (m, 2H); 7.42–7.51 (t, 1H); 7.51–7.81 (m, 5H); 7.96 (s, 2H); 8.13 (s, 1H); 8.39 (s, 1H); 9.59 (s, 1H); 9.72 (s, 1H); 10.45 (s, 1H); 10.95 (s, 1H).
MS: [M=H]+ at 694,696; measured: 694.1681; theory for $C_{37}H_{27}C_1F_2N_5O_5$: 694.1669.

EXAMPLE 11

Reaction of (S)-N-[2-[[1-(chloromethyl)-I 6-dihydro-5-hydroxy-8-methylbenzo[1,2-b:4,3-b']dipyrrol-3(2-yl]carbonyl]-1H-indol-5-yl]-6-(diethylamino)-2-benzofurancarboxamide with isocyanates A 0.015 mmol quantity of (S)-N-[2-[[1-(chloromethyl)-1,6-dihydro-5-hydroxy-8-methylbenzo[1,2-b: 4,3-b']dipyrrol-3(2-yl]carbonyl]-1H-indol-5-yl]-6-(diethylamino)-2-benzofurancarboxamide (U-76073) is dissolved in the dark in 1.0 ml of freshly distilled THF. Two equivalents of the isocyanate and 5 equivalents of triethylamine is added and the reaction mixture stirred from 1 hour to 30 days under nitrogen in the dark at room temperature. The reaction progress is checked by HPLC or TLC. When completed, the crude product is chromatographed over 100 to 1 silica gel, eluting with acetone-hexane. 0.5/1.0 ml fractions are collected and analyzed by TLC. The fractions containing product are combined and evaporated to yield the desired compound.

EXAMPLE 11A

Preparation of (S)-8-(chloromethyl)-6-[[5-[[[6-(diethylamino)-2-benzofuranyl]carbonyl]amino]-1H-indol-2-yl]carbonyl]-3,6,7,8-tetrahydro-1-methylbenzo[1,2-b 4,5-b']dipyrrol-4-yl ester, 2,2-dimethyl-propanoic acid (Cpd #11A)

A 9 mg (0.016 mmol) quantity of (7bR)-6-diethylamino)-N-[2-[(4,5,8,8a-tetrahydro-7-methyl-4-oxocyclopropa[c]pyrrolo[3,2-e]indol-2(1H)-yl) carbonyl]-1H-indol-5-yl]-2-benzofurancarboxamide is dissolved in 150 microL of dry pyridine at 25° C. To this solution is added 6 microL of pivaloyl chloride. After 15 min the reaction is treated with 1 drop of water and then evaporated under vacuum. The residue is placed on top of a 1.5 g silica gel column which is then eluted with acetone-hexane (40/60) followed by pure acetone. The 1 ml fractions (5–28) containing the title compound were combined to give 8 mg of the title compound.

TLC (silica gel): 40% acetone—60% hexane; Rf 0.44.
NMR: DMSO, TMS.
1.10–1.19 (t, 6H); 1.39 (s, 9H); 2.41 (s, 3H); 3.38–3.49 (q, 4H); 3.69–3.78 (dd, 1H); 3.95–4.04 (dd, 1H); 4.14–4.26 (t, 1H); 4.56–4.64 (m, 1H); 4.67–4.79 (t, 1H); 6.77–6.84 (m, 2H); 7.17 (s, 1H); 7.24 (s, 1H); 7.43–7.50 (d, 1H); 7.51–7.62 (m, 3H); 7.80 (s, 1H); 8.21 (s, 1H); 10.15 (s, 1H); 10.87 (s, 1H); 11.66 (s, 1H).

MS: [M=H]+ at 694,696; [M]+at 693, 695. Measured: 694.2792, theory for $C_{39}H_{41}Cl_1N_5O_5$: 694.2796. Other fragment ions: 658, 610, 574, 374, 216.

EXAMPLE 11B

Preparation of (S)-N-[2-[[1-(chloromethyl)-1,6-dihydro-8-methyl-5-[[(phenylamino)carbonyl]oxy]benzo[1,2-b 4,3-b']dipyrrol-3(2H)-yl]carbonyl]-1H-indol-5-yl]-6-(diethylamino)-2-benzofurancarboxamide (Cpd #11B)

Following the general procedure of Example 11, 4 mg (0.03 mmol) of phenyl isocyanate and 0.7 mg (0.007 mmol) triethylamine is added to a 9 mg (0.015 mmol) quantity of (S)-N-[2-[[1-(chloromethyl)-1,6-dihydro-5-hydroxy-8-methylbenzo [1,2-b: 4,3-b']dipyrrol-3 (2-yl]carbonyl]-1H-indol-5-yl]-6-(diethylamino)-2-benzofurancarboxamide dissolved in the dark in 1 ml of THF. The reaction is stirred in the dark for 36 hr under nitrogen at room temperature. The crude product is chromatographed over 2 g silica gel, eluting with acetone-hexane (40/60) to (80/20). The fractions containing the title compound are combined and evaporated.

TLC (silica gel): 40% acetone—60% hexane; Rf 0.49.
NMR: DMSO, TMS.
1.09–1.19 (t, 6H); 2.42 (s, 3H); 3.38–3.48 (q, 4H); 3.7–3.8 (t, 1H); 3.96–4.05 (d, 1H); 4.15–4.26 (6, 1H); 4.56–4.66 (m, 1H); 4.71–4.81 (t, 1H); 6.76–6.84 (m, 2H); 7.00–7.10 (t, 1H); 7.15–7.23 (d, 2H); 7.30–7.42 (dd, 2H); 7.43–7.50 (d, 1H); 7.51–7.62 (m, 5H); 7.95 (s, 1H); 8.20 (s, 1H); 10.15 (s, 1H); 10.36 (s, 1H); 11.21 (s, 1H); 11.69 (s, 1H).

MS: [M=H]+at 729,731; Measured: 729.2587. Theory for $C_{41}H_{38}ClN_6O_6$: 729.2592. Other fragment ions: 609,574, 374, 236, 216, 201, 187.

The starting compounds are known or can be readily prepared by known methods. See M. A. Warpehoski, Tet. Lett., 27, 4103 (1986); W. W. Wierenga, J. Am. Chem. Soc., 103, No. 18, 1981; and D. G. Martin, J. Antibiotics 1985, 38, 746. The spirocyclopropylcyclohexadienyl compounds of Formula I can be prepared by the procedures and methods disclosed in copending U.S. patent application Ser. No. 894,314, filed Aug. 7, 1986, and incorporated herein by reference, and EP Application 0 154 445.

The natural isomers and/or the racemic spirocyclopropylcyclohexadienyl compounds of Formula I can also be prepared by the chemical steps shown in Chart B. The process details of each step are given in the non-limiting procedures which appear as Examples 46–50 of U.S. patent application Ser. No. 894,314, filed Aug. 7, 1986, and EP Application 0 154 445.

The natural isomers and/or the racemic spirocyclopropylcyclohexadienyl compounds of Formula I can also be prepared by the chemical steps shown in Charts B1 and B2. From the 1,1-dimethylethyl ester of (S)-1-(chloromethyl)-1,6-dihydro-2-Z-5-hydroxy-8-W-benzo[1,2-b:4,3-b']dipyrrole-3(2H)-carboxylic acid, the natural isomers of Formula I can be prepared in two-step, highly flexible synthesis which allows the conversion of essentially any carboxylic acid to the coupled product as its hydrochloride which then can be converted to the natural spirocyclopropylcyclohexadienyl compound (Formula I) in a single step. The process details of each step are given in the non-limiting procedures which follow. Ms means mesyl; Bzl means benzyl; and Boc means t-butoxy carbonyl (COO-t-butyl).

Chart B1-Step 1: The starting material 1,2,3,6-tetrahydro-8-methyl-5-(phenylmethoxy)benzo[1,2-b:4,3-b']dipyrrole-1-methanol N- methanesulfonate is stable, easily handled and described by M. A. Warpehoshki, Tet. Lett., 27, 4103 (1986).

1.0 g (2.6 mmol) of the starting material, in 50 ml freshly distilled THF and 50 ml toluene under nitrogen, is reduced with the dropwise addition and stirring of (5.0 ml, 17 mmol) Red-Al (3.4M solution of bis(2-methoxy-ethoxy)aluminum hydride in toluene). The solution is quickly heated under a flow of nitrogen, allowing the escape of the THF until the internal temperature reaches 85° C. The reaction is allowed to continue at 85° C. for 15 minutes and then cooled in an ice bath and carefully treated with 50 ml 15% potassium carbonate. The reaction mixture is then partitioned between waterethylacetate through which nitrogen is blown. The layers are separated and the aqueous layer reextracted with ethylacetate. The organic layers are combined, dried over sodium sulfate and evaporated under vacuum. The residual oil is treated with methylene chloride and reevaporated leaving the crude amine 2.

Step 2: The amine product of Step 1 is unstable in air and is therefore stirred at room temperature under nitrogen in 10 ml freshly distilled THF, 0.375 ml triethylamine and 700 mg of 2-(tert-butoxycarbonyloxyimino)-2-phenylacetonitrile (BOC-ON) for 3.5 days or until TLC shows the reaction to be complete. The reaction mixture is coated on 20g silica gel and placed on top of a 180g silica gel column made up in ethylacetate-hexane (10/90). The column is eluted with 900 ml ethylacetate-hexane (10:90) and 500 ml each of the following ethylacetate-hexane combinations 20:80, 30:70, 40:60; and 50:50. Fractions of 40ml are collected, analyzed by TLC and the fractions (63–73) containing compound 3 collected.

NMR: (CDCl₃, TMS, δ) 1.6; 2.3; 3.4–4.4; 5.15; 6.9; 7.2–7.8; 8.5.

Step 3A: 120 mg (0.29 mmol) of the product of step 2, 1,1-dimethylethyl ester of 1-(hydroxymethyl)-1,6-dihydro-8-methyl-5-(phenylmethoxy)-benzo[1,2-b:4,3-b']dipyrrole-3(2H) -carboxylic acid, is stirred at 0° C. under nitrogen in 2 ml pyridine. Syringe in 100 μl mesyl chloride and leave to warm at room temperature for 6 hours. The reaction mixture is cooled to 0° C. and a few drops of 5% sodium bisulfate added. After a few minutes the reaction mixture is partitioned between 5% sodium bisulfate and methylene chloride. The layers are separated and the aqueous layer reextracted with methylene chloride. The organic layers are washed with water, dried over sodium sulfate, combined and evaporated under vacuum to yield the crude product 6.

NMR: (CDCl₃, TMS, δ) 1.6; 2,4; 2.8; 3.6–4.6; 5.1; 6.9; 7.2–7.7; 8.4.

Step 3B: 242 mg (0.59 mM) of the product of step 2, 1,1-dimethylethyl ester of 1-(hydroxymethyl)-1,6-dihydro-8-methyl-5-(phenylmethoxy)-benzo[1,2-b:4,3-b']dipyrrole-3(2H)-carboxylic acid, is dissolved in distilled THF (2.4 ml) and absolute ethanol (25 ml). The compound is hydrogenalized over 10% palladium on carbon (192 mg) at 42 PSI for 50 minutes. The reaction is filtered through diatomaceous earth, washing with absolute ethanol. Evaporation yields compound 4, 1,1-dimethylethyl ester of 1-(hydroxymethyl)-1,6-dihydro-8-methyl-5-hydroxy-benzo[1,2-b:4,3-b']dipyrrole-3(2H)-carboxylic acid.

NMR: (Acetone-d₆, TMS, δ) 1.55; 2.39; 2.98–4.07; 4.07–4.48; 7.05; 7.40; 8.81; 9.79.

TLC (Silica gel GF): R$_f$=0.60 in ethyl acetate-hexane (50/50).

Step 4A: 200mg (0.29 mmol max) of the product of step 3A, 1,1-dimethylethyl ester of 1-(methanesulfonyloxymethyl) -1,6-dihydro-8-methyl-5-(phenylmethoxy)-benzo[1,2-b:4,3-b']dipyrrole-3(2H)-carboxylic acid, the crude mesylate, is stirred under nitrogen at 80° C. in 3 ml DMF and 40 mg lithium chloride for 25 minutes, when TLC shows the reaction to be complete. The reaction mixture is cooled to room temperature, and partitioned between methylene chloride and water. The layers are separated and the aqueous layer reextracted with methylene chloride. The organic layers are combined, dried over sodium sulfate and evaporated under high vacuum. The crude product is chromatographed over 10 g silica gel, eluting with ethyl acetate-hexane (20:80). Fraction of 5 ml are collected and the product found by TLC in fractions 7–17, which upon combining and evaporating yield compound 7, 1,1-dtmethylethyl ester of 1-(chloromethyl) -1,6-dihydro-8-methyl-5-(phenylmethoxy)-benzo[1,2-b:4,3-b']dipyrrole-3(2H)-carboxylic acid.

MS: [M+H]⁺ at 427,429; [M]⁺ at 426,428. Measured: 426.1721; theory for C₂₄H₂₇ClN₂O₃: 426.1710.

NMR: (CDCl₃, TMS, δ) 1.6; 2.4; 3.2–4.5; 5.2; 7.0; 7.3–7.7; 8.3.

Step 4B: A 145 mg quantity (0.455 mM) of the diol 4, 1,1-dimethylethyl ester of 1-(hydroxymethyl)-1,6-dihydro-8-methyl-5-hydroxy-benzo[1,2-b:4,3-b']dipyrrole-3(2H)-carboxylic acid, is treated with freshly distilled THF (7.4ml), triphenylphosphine (189.5 mg, 0.722 mM), and diethylazodicarboxylate (110 μl, 0.700 mM) under nitrogen. The reaction is stirred 80 minutes at room temperature and adsorbed onto 3g of silica gel and chromatographed on a 27g silica gel column in distilled THF-hexane (45/55). Fifteen ml fractions are collected. The product fractions are collected, evaporated and triturated with ethyl acetate to give compound 5, 1,1-dimethylethyl eater of 4,5,8,8a-tetrahydro-7-methyl-4-oxocyclopropa[c]pyrrolo(3,2-e)indol-2(1H)-carboxylic acid.

NMR: (CDCl₃+CD₃OD, TMS, δ) 1.08–1.42; 1.58; 1.84–2.17; 2.80–3.14; 3.29–3.48; 6.73; 6.93.

TLC (Silica Gel GF): R$_f$=0.36 in ethyl acetate-hexane (60/40), Rf=0.5 in THF-hexane (50/50).

Step 5A: A 110 mg quantity (0.26 mM) of the product of Step 4A, 1,1-dimethylethyl ester of 1-(chloromethyl)-1,6-dihydro-8-methyl-5-(phenylmethoxy)-benzo[1,2-b:4,3-b']dipyrrole-3(2H)-carboxylic acid, is stirred at room temperature under nitrogen in 2 ml freshly distilled THF and 2 ml methanol. 120 mg 10% Pd/C (palladium on charcoal) and 130 mg ammonium formate is added. After TLC shows the reaction mixture to be complete, the reaction mixture is filtered, and the solid washed with freshly distilled THF. The combined filtrate and wash is partitioned between ethyl acetate and brine (saturated aqueous sodium chloride solution), the layers separated and the aqueous layer reextracted with ethyl acetate. The organic layers are combined, dried over sodium sulfate and evaporated yield (BOC)CPI hydrochloride, 1,1-dimethylethyl ester of 1-(chloromethyl)-1,6-dihydro-5-hydroxy-8-methyl-benzo[1,2-b:4,3-b']dipyrrole-3(2H)-carboxylic acid.

NMR: (CDCl₃, d₆-acetone, TMS, δ) 1.6; 2.4; 3.3–4.4; 7.1; 7.4; 8.9; 9.7.

MS: measured 336.1230. Theory for C₁₇H₂₁ClN₂O₃ 336.1241.

Chart B2—Step 1: 16.1 mg (0.048 mmol) of (BOC)-CPI hydrochloride, 1,1-dimethylethyl ester of (S)-1-(chloromethyl)-1,6-dihydro-5-hydroxy-8-methyl-benzo[1,2-b:4,3-b']dipyrrole-3(2H)-carboxylic acid is dissolved in ethyl acetate under an inert atmosphere (nitrogen), treated with 2 ml of an HCl-saturated ethyl acetate solution and the reaction run at room temperature for 40 minutes. The reaction mixture is evaporated to dryness under vacuum, then the flask recharged with nitrogen. The solid is dissolved in methylene chloride and evaporated again to remove traces of acid. The crude amine salt is used immediately in the next step.

Step 2: The crude amine salt of step 1A is stirred in dry dimethylformamide (0.95 ml) with 25.2 mg (0.048 mmol) of 7-[[7-(aminocarbonyl-3,6,7,8-tetrahydro-5-hydroxy-4-methoxybenzo-[1,2-b:4,3-b,]dipyrrol-2-yl]carbonyl]-3,6,7,B-tetrahydro-5-hydroxy-4-methoxybenzo[1,2-b:4,3-b']dipyrrole-2-carboxylic acid, (PDE1 dimer, see DG Martin, J Antibiotics, 1985, 38, 746) and 9.4 m$_E$ (0.049 mmol) 1-ethyl-3(3-dimethylaminopropyl)-carbodiimide hydrochloride (EDC). The reaction is maintained under nitrogen at room temperature for two hours, diluted with water and centrifuged. The liquid is removed and the solid washed with water. After drying under vacuum overnight, the solid is absorbed onto 0.76 g of silica gel from DMF and placed on a 5 g silica column and eluted with DMF-acetone-methylene chloride (8-17-75). Fractions of 3 ml are collected and the desired product isolated from the fractions (8–29).

NMR: (DMSO-d7, TMS, δ) 1.24; 2.36; 3.27; 3.58; 3.83; 3.90; 3.83–4.12; 4.41–4.79; 6.88–7.10; 7.67; 7.55; 9.80; 10.72; 10.93; 11.37.

Step 3: 10 mg (0.013mmol) of the product of step 2A having the S stereochemistry is stirred under nitrogen with 4 ml of acetonitrile, 1 ml water, and 1 ml triethylamine for 25 minutes. The reaction mixture is partitioned between ethyl acetate and water. The aqueous layer is extracted with additional ethyl acetate and the combined organic layer are washed with water, dried over sodium sulfate and evaporated to yield the product, natural CC-1065.

NMR (DMSO-d6, TMS, $\delta$): 0.68–1.35; 1.47; 2.005; 3.823; 3.863; 4.04; 4.37; 4.70; 6.45; 6.8–7.2; 11.06; 11.38; 11.54.

Following the procedures of Steps 1,2 and 3 (Chart B2) and starting with 1,1-dimethylethyl ester of (R)-1-(chloromethyl)-1,6-dihydro-5-hydroxy-B-methyl-benzo[1,2-b: 4,3-b']dipyrrole-3 (2H) -carboxylic acid, ent-CC-1065 is prepared. CD in DMF: nm(molarellipticity) 330 (+32,000), 290(−42,000).

All the compounds of the subject invention have UV absorption in the range of 200 nm to 380 nm. Thus, novel compounds of the subject invention (Formula I') are useful as UV absorbents in technical and industrial areas, as follows:

(a) textile materials, for example, wool, silk, cotton, hemp, flax, linen and the like;
(b) natural or synthetic resins.

Depending on the nature of the material to be treated, the requirements with regard to the degree of activity and durability, and other factors, the proportion of the light screening agent to be incorporated in the material may vary within fairly wide limits, for example, from about 0.01% to about 10%, and, advantageously, 0.1% to 2% of the weight of the material which is to be directly protected against the action of UV rays.

The compounds of Formula I' are particularly useful as antitumor agents. Examples of compounds of Formula I' demonstrate antitumor activity in P388 leukemic mice, and also show significant activity in the L1210 leukemia and B16 melanemia murine test systems. These murine test systems are predictive for clinically useful human antitumor agents (see, for example, A. Geldin et al, European J. Cancer, Vol. 17, pp 129–142, 1981; J. M Vendetti, Cancer Treatment Reports, Vol. 67, pp. 767–772, 1983; and J. M. Vendetti et al, Advances in Pharmacology and Chemotherapy, Vol. 20, pp. 1–20, 1984), and, therefore, the compounds of the subject invention (Formula I') will be useful in the control and treatment of susceptible neoplastic (cancer) diseases in humans when given, for example, intravenously in doses of 0.001 to about 10 mg/kg of body weight per day, the exact dose depending on the age, weight, and condition of the patient, and on the frequency of administration.

The compounds of Formula I' are advantageous over their cyclized counterpart. (Formula I) and its ring opened phenol synthetic precursors (Formula I' wherein Y=H and X=Br, Cl, I, or OSO$_2$CH$_3$) because of improved solubility, increased stability, improved half life in the animal or human, improved bodily distribution, and improved therapeutic index over the cyclized counterparts and their alcohol synthetic precursors. The compounds of Formula I' are effective when administered intravenously (IV) in fluid solutions by bolus injection or by infusion. The preferred doses are 5 microgram/kg to 1000 microgram/kg by bolus injection and 0.002 to 200 microgram/kg/min by infusion. The exact dose will vary depending on the particular compound as well as the age, weight, route of administration, and physical condition of the patient, and on the frequency of administration.

Illustrative in vivo testing data on the compounds of Formula I' and comparison with their spirocyclopropyl analogs (Formula I) and chlorophenol analogs are presented in Table 1. The structures of the various compounds of Formula I' are presented in Table 2 and their spirocyclopropropylcyclohexadienyl and chlorophenol analogs are presented in Table 3.

The compounds of Formula I' show several favorable biological effects. The compounds of Formula I' generally show activity over an additional dose level compared with the corresponding compounds of Formula I (data not shown). In addition, the compounds of Formula I' often show superior activity. For example see Table 1, comparison of entry 1 with entries 26 and 29 shows that the acetate Cpd #1 given IV is superior vs IP administered L1210 leukemia when compared with its SCPCH precursor U-71184 and its chlorophenol precursor U-73903. Similarly, the CC-1065 derived decanoate Cpd #3 (entry 16) and hexanoate Cpd #5 (entry 25) when administered IP on days 1, 5, and 9 show superior activity to CC-1065 (U-56314 entry 36) also administered by the same dose schedule. Although a direct comparison is not available in all cases, the table strongly indicates a superiority of the prodrugs by the oral route of administration. Thus, Cpd #1 (entry 3) given orally on days 1–5 has superior activity vs IP P388 compared to U-71184 (entry 28) and U-73903 (entry 31) given by the same route and schedule. While there is no direct comparison for the excellent oral activity of Cpd #2A (entry 7) or Cpd #2E (entry 13), it should be noted that generally L1210 is a more difficult system than the P388 system and that vs the various leukemias U-71184 has generally shown slightly superior activity to U-73975. Thus, it is quite impressive that oral Cpd #2A (entry 7) and oral Cpd #2E (entry 13) show superior activity vs L1210 compared with the oral activity of Cpd #1 vs L1210 (entry 2) and vs P388 (entry 3). The activity difference is even greater when compared with the oral activity of U-71184 and U-73903 vs P388 (entries 28 and 31).

The results set forth in Tables 1 and 4 were obtained using standard well known procedures (In Vivo Cancer, Models, NIH Publication No. 84–2635, 1984).

T/C refers to median life span of treated mice divided by median life span of control mice times 100.

The compounds of formula I', where X is halogen and Z is hydrogen, are useful as antibacterial agents. These compounds are useful to control the proliferation of susceptible microbes in various environments using standard microbiological techniques. Such environments include laboratory benches in a microbiological laboratory which can be cleansed with a formulation of compounds of formula I', where X is halogen and Z is hydrogen; dental utensils contaminated with *S. aureus*, and the like.

Relative to the compounds claimed in this case, the O-protected compounds described in EP 154445 are significantly less biologically effective, particularly in terms of antitumor potency. The O-protected compounds of Formula II in EP 154445 are important as synthetic intermediates necessary to make the biologically active compounds of EP 154445 (compounds of Formula I or of Formula II when R$_1$ is H). The O-protecting groups in EP 154445 are chemically stable and only removable under specific chemical conditions. More importantly, the O-protected compounds of EP 154445 are not readily cleaved under physiological conditions to the active species and are therefore much less effective than the compounds of this case. In general the groups on the phenol in the compounds of this case are too labile to function as good protecting groups since they would be cleaved prematurely (such as at the RedAl step (Chart B1, step 1 ) in the synthesis). In accord with this, the groups on the phenol in this case appear to be labile even to physiological conditions, thus being pro-drugs which can be converted ultimately to the highly biologically active compounds of Formula I of EP 154445.

For a specific example, the O-benzylated product of Example 48, step 5 at page 42 (and step 5, chart IV at page 87) of U.S. patent application Ser. No. 894,314, filed Aug. 7, 1986. (See also, EP Application 0 154 445) has less than 1/10 the potency of any of the corresponding O-acylated compounds (2A through 2G in Table 2).

Similarly, U-69815 (page 54 of U.S. patent application Ser. No. 894,314, filed Aug. 7, 1986, and EP Application 0 154 445) has less than 1/20 the potency of the corresponding O-acetylated compound (compound 1 of Table 2).

GENERAL FORMULAE CHART

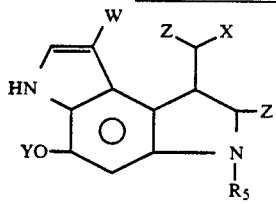

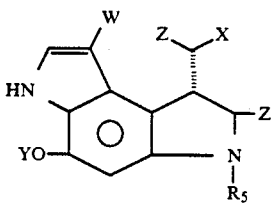

-continued
GENERAL FORMULAE CHART

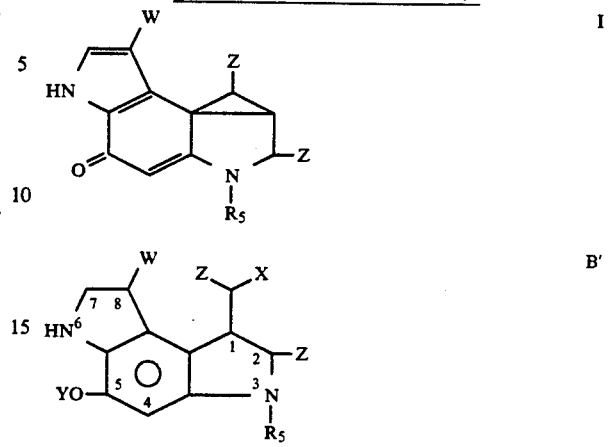

CHART A

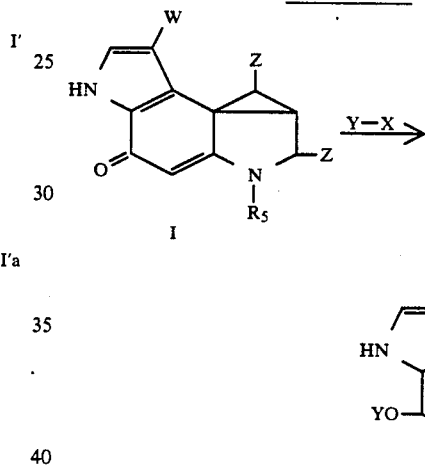

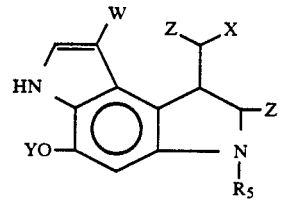

CHART A'

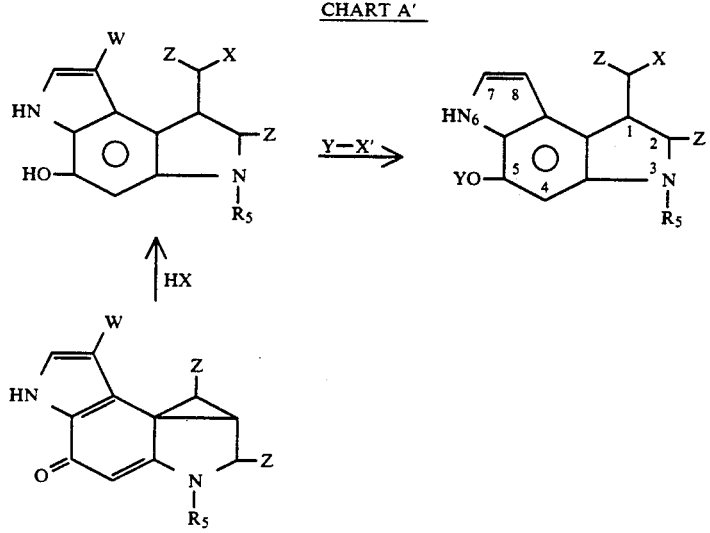

CHART A''
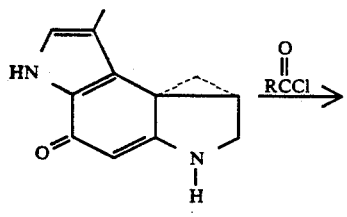
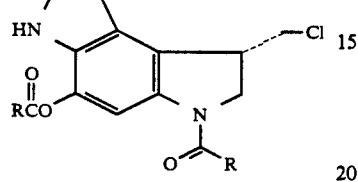
Example 7   R = n-C₅H₁₁ = n-pentyl
Example 8   R = —⟨phenyl⟩—Cl = 4-chlorophenyl
CHART A'''
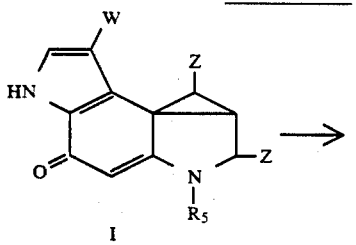
I
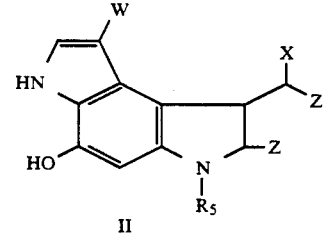
II
-continued
CHART A'''
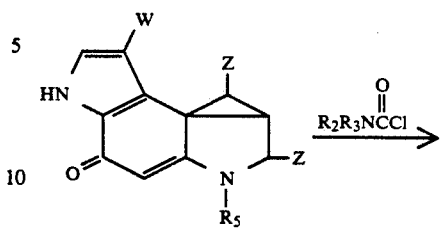
I
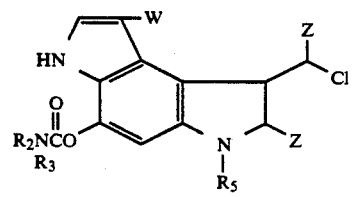
II
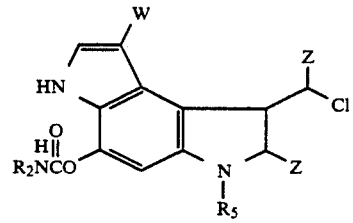
CHART B
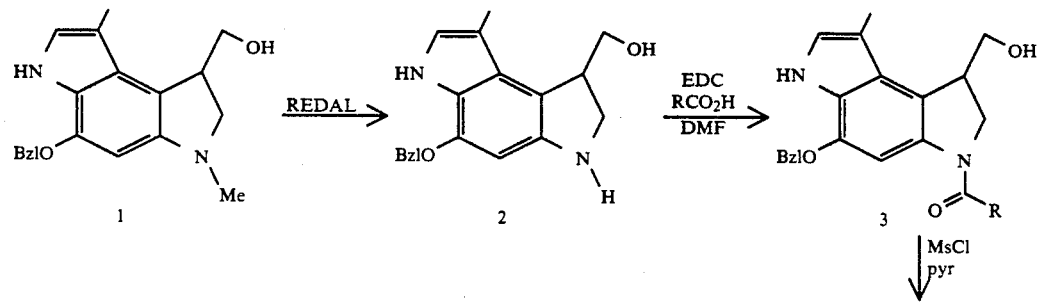

CHART B
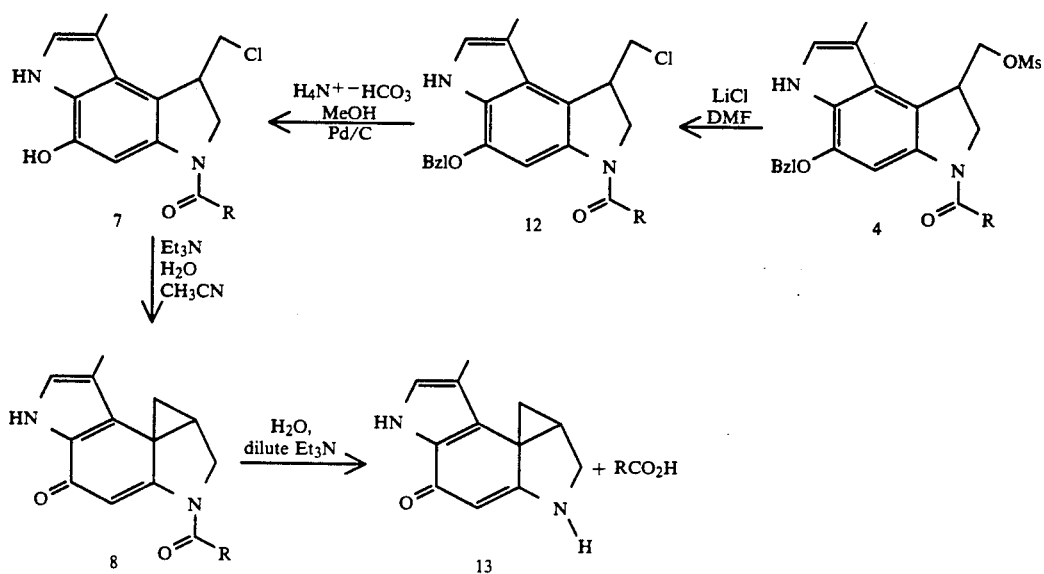
CHART B1
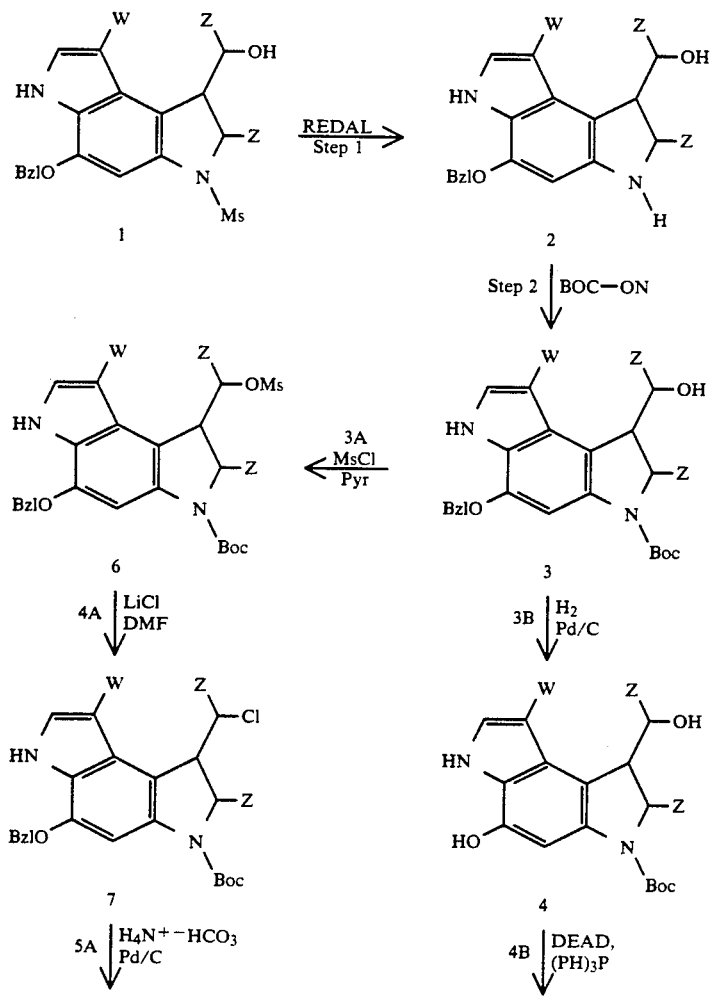

CHART B1

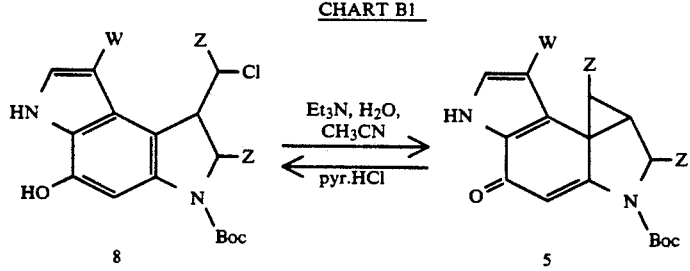

Bzl = CH2C6H5

Boc = $\overset{O}{\overset{\|}{-C}}$—O-t-Bu

CHART B2

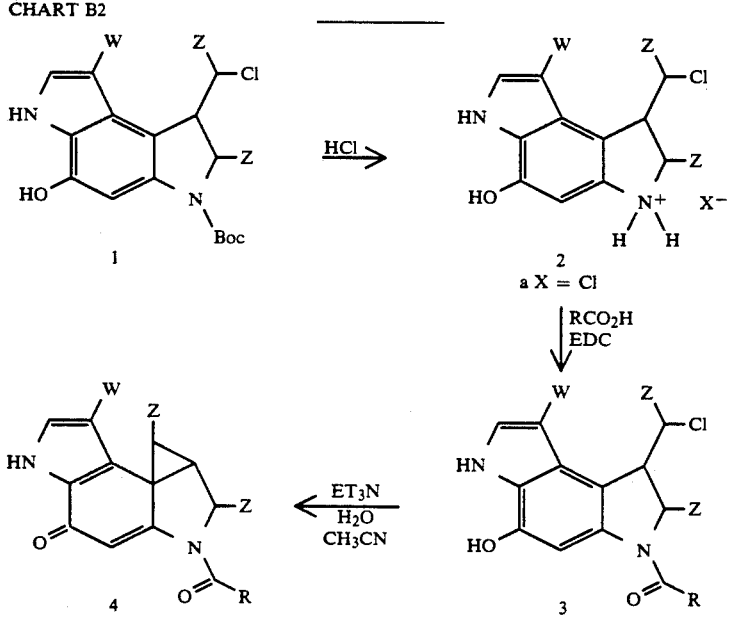

a X = Cl

CHART C (i) —C(O)—R6 where R6 is H, alkyl (C1-C20), —CCl3, CF3, or NH2, (ii)
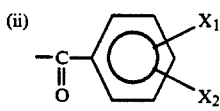

where X1 and/or X2 is H, CH3, OH, OCH3, NO2, NH2, (NHNHAc) NHNHC(O)CH3, (NHBz) NHC(O)C6H5, or halogen;

(iii) acyl derivatives (—C(O)—CHNH2—R7) of the 20 natural amino acids where R7 is the amino acid residue of glycine, alanine, valine, isoleucine, leucine, serine, threonine, aspartic acid, glutamic acid, lysine, arginine, asparagine, glutamine, cysteine, methionine, tryptophan, phenylalanine, tyrosine and histidine or proline; and their common salts selected from Na+, K+, NH4+, HCl, H3PO4 and (HOAc) HOC(O)CH3;

(iv) —C(O)—CH2CH2—CO(C)−M+ is Na, K, NH4, or N(CH3)4;

(v)

-continued
CHART C

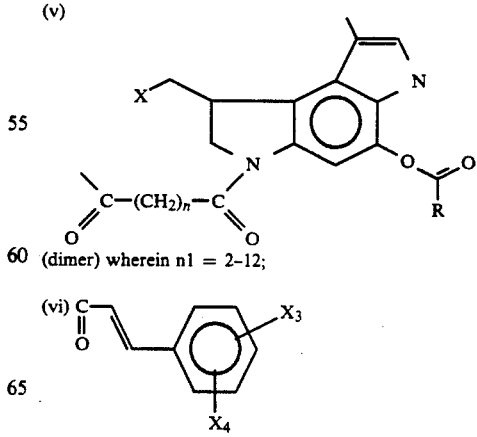

(dimer) wherein n1 = 2-12;

(vi) where X3 and/or X4 = H, OH, OCH3;

-continued
CHART C (vii) 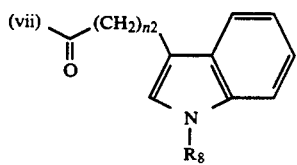

where n2 = 1-3; and R8 is H, CH3 or C2H5;

(viii) 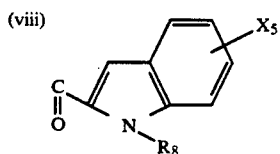

where X5 = H, OH, OCH3, NO2, NH2, (NHAc) NHC(O)CH3, NHC(O)NH2; (NHBz) NHC(O)C6H5; NH—CN; and R8 has the meaning defined above;

(ix) 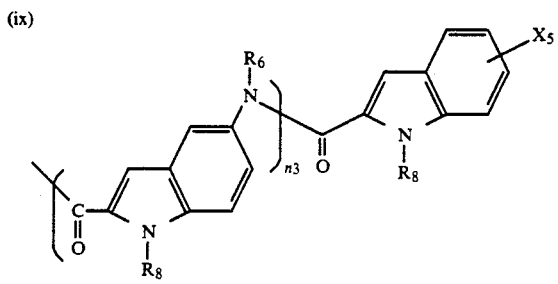

where n3 = 1, 2, or 3; and R8, R6 and X5, have the meanings defined above;

(x) 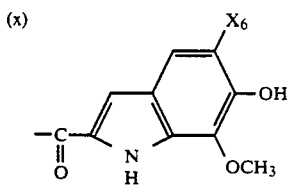

where $X_6$ = H, NO2, NH2, NHAc, NHC(O)NH2;

(xi) 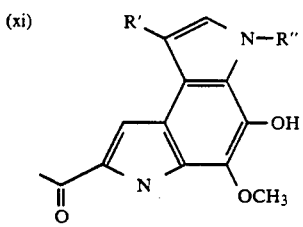

wherein R' is H or CH3S— and R" is NH2(C)O— or CH3C(O)—;

(xii) 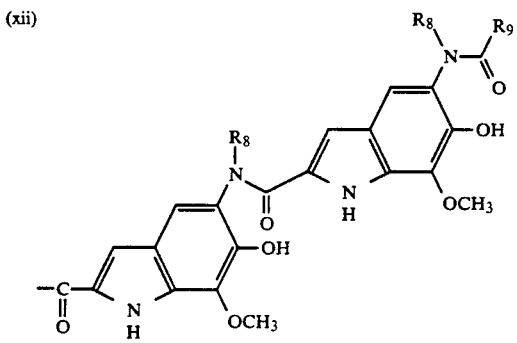

where R8 has the meanings defined above, and R9 is —CH3 or —NH2;

-continued
CHART C (xiii) 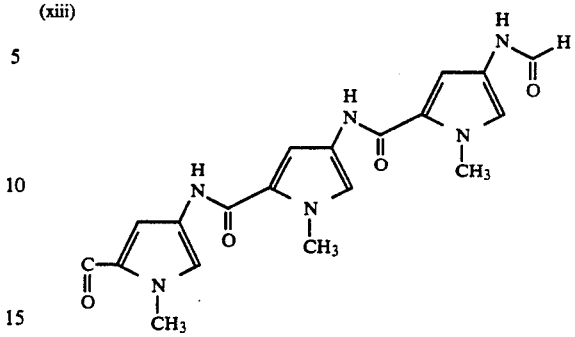

(xiv) 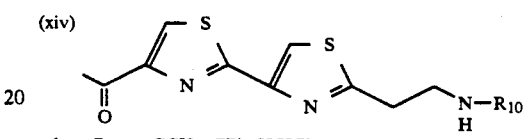

where $R_{10}$ = CCH3, CPh, H.HCl;
         ||    ||
         O    O (xv) —C(O)+R11+C(O)—X7+CH2CH2—X7)n4—H
where R11 = CH2CH2, CH=CH; and X7 = O, NH, and n4 = 1-4, and the HCl and MeI salts for X7 = NH;

(xvi)
—C(O)+R11+C(O)—X7+CH2CH2—X7)n4—C(O)+R11+C(O)—
(dimer) where R7 and R11 and n4 have the meanings defined above;

(xvii) 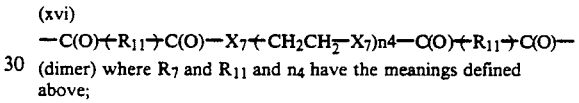

where X8 is —O—, —S—, NH; X9 is —CH= or —N=; and X5 has the meanings defined above;

(xviia) 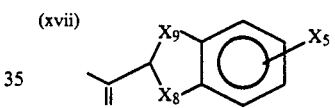

where X9 and X8 have the meanings defined above; and Y1 and/or Y2 = H, halo, C1-C4-alkyl, C1-C3-alkoxy, C2-C6-dialkylamino, nitro, aminocarbonylalkyl(C1-C10), hydroxy, amino (—NH2), —NHCONH2, —NHAc (NHCOCH3) or —NHBz (—NHC(O)C6H5);

(xviib) 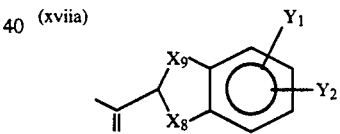

where X8, Y1 and Y2 have the meanings defined above;

(xviii) 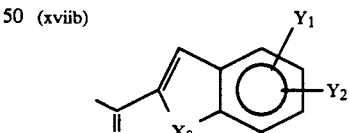

where X5 has the meaning defined above;

(xix) 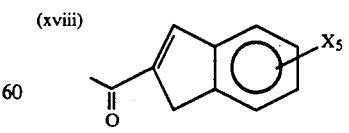

-continued
CHART C where $X_{10}$ is —CH= or —N= and $X_7$ is SH, $NH_2$, OH, H, or NHAc;

(xx)

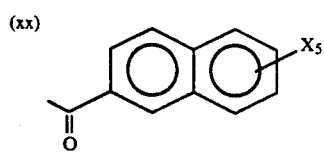

where $X_5$ has the meaning defined above;

(xxi)

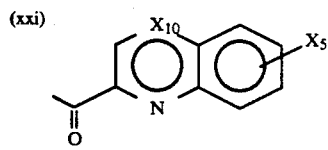

where $X_5$ and $X_{10}$ have the meanings defined above; and (xxii)

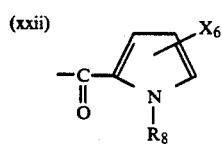

where $X_6$ and $R_8$ have the meanings defined above.

CHART D

| | |
|---|---|
| ii + ii | ii + vi |
| ii + viii | ii + ix |
| ii + xvii | ii + xviii |
| ii + xix | ii + xx |
| ii + xxi | ii + xxii |
| vi + vi | vi + viii |
| vi + ix | vi + x |
| vi + xvii | vi + xviii |
| vi + xix | vi + xx |
| vi + xxi | vi + xxii |
| viii + viii | viii + ix |
| viii + xviib | viii + xviia |
| viii + x | xviii + xvii |
| viii + xviii | viii + xix |
| viii + xx | viii + xxi |
| viii + xxii | ix + ix |
| ix + x | ix + xvii |
| ix + xx | ix + xxi |
| ix + xxii | x + x |
| x + xvii | x + xviii |
| x + xix | x + xx |
| x + xxi | x + xxii |
| xvii + xvii | xvii + xviii |
| xviia + xviia | xvii + xviia |
| xvii + xix | xvii + xx |
| xvii + xxi | xvii + xxii |
| xviii + xviii | xviii + xvii |
| xviii + xix | xviii + xx |
| xviii + xxi | xviii + xxii |
| xix + xix | xix + xx |
| xix + xxi | xix + xxii |
| xx + xx | xx + xxi |
| xx + xxii | xxi + xxi |
| xxi + xxii | xxii + xxii |

CHART E $R_5$ = xix + xix =

CHART E -continued $R_5$ = xix + xix =

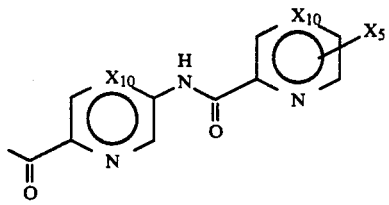

$R_5$ = xviii + viii =

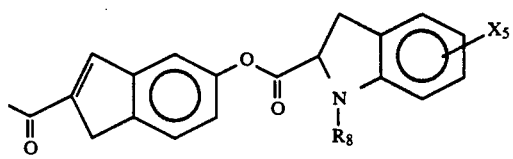

$R_5$ = ii + xxi =

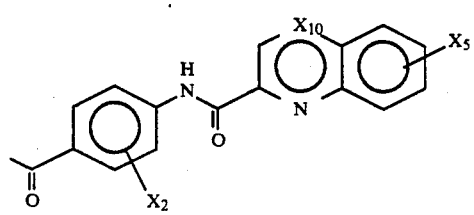

$R_5$ = viii + xviib =

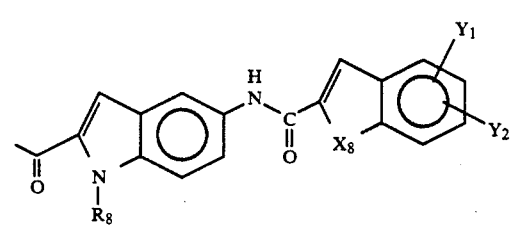

$R_5$ = viii + xviia =

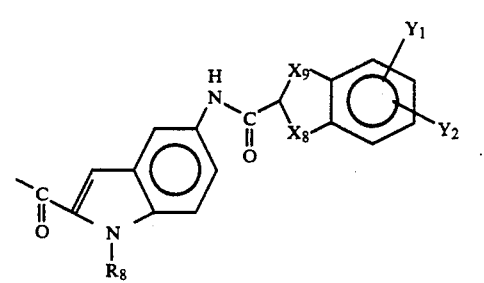

$R_5$ = viii + viii =

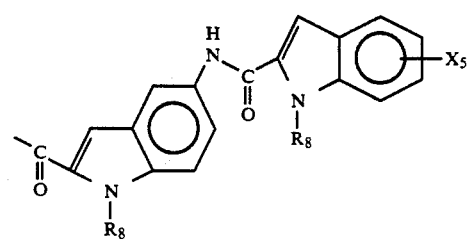

TABLE 1
Comparison of the in vivo Biological Activity of Compounds of Formula I' and I.

| ENTRY # | CPD # | TEST | RT ADMIN TUM/DRUG | DAYS OF DOS | MG/KG | T/C | 30 DAY SURVIV |
|---|---|---|---|---|---|---|---|
| | | | Prodrugs | | | | |
| 1 | 1 | L1210 | IPIV | 1 | 0.20 | * | 3/6 |
| 2 | 1 | L1210 | IP-ORAL | 1,5,9 | 0.60 | 128 | — |
| 3 | 1 | P388 | IP-ORAL | 1-5 | 0.16 | 120 | — |
| 4 | 1 | P388 | IPIV | 1 | 0.20 | * | 4/6 |
| 5 | 2A | L1210 | IPIV | 1 | 0.20 | 200 | — |
| 6 | 2A | L1210 | IPIV | 1 | 0.40 | 181 | — |
| 7 | 2A | L1210 | IP-ORAL | 1,5,9 | 0.60 | 175 | — |
| 8 | 2A | P388 | IPIV | 1 | 0.20 | 263 | 2/6 |
| 9 | 2B | L1210 | IPIV | 1 | 0.20 | 188 | — |
| 10 | 2C | L1210 | IPIV | 1 | 0.20 | 200 | 1/6 |
| 11 | 2D | L1210 | IPIV | 1 | 0.20 | 194 | — |
| 12 | 2E | L1210 | IPIV | 1 | 0.20 | 182 | — |
| 13 | 2E | L1210 | IP-ORAL | 1 | 0.20 | 150 | — |
| 14 | 2F | L1210 | IPIV | 1 | 0.20 | 188 | — |
| 15 | 3 | L1210 | IPIV | 1 | 0.20 | 257 | |
| 16 | 3 | P388 | IPIP | 1,5,9 | 0.05 | * | 4/6 |
| 17 | 3 | B16 | IPIV | 1 | 0.10 | 175 | — |
| 18 | 3 | B16 | IPIV | 1 | 0.20 | 190 | — |
| 19 | 3 | LLUNG | SCIV | 1 | 0.10 | 142 | — |
| 20 | 3 | LLUNG | SCIV | 1 | 0.05 | 102 | — |
| 21 | 6 | L1210 | IPIV | 1 | 0.40 | 200 | — |
| 22 | 2G | L1210 | IPIV | 1 | 0.10 | 171 | — |
| 23 | 4 | L1210 | IPIV | 1 | 0.20 | 243 | — |
| 24 | 4 | B16 | IPIV | 1 | 0.40 | 181 | — |
| 25 | 5 | P388 | IPIP | 1,5,9 | 0.05 | 255 | 2/6 |
| | | | U-71184 and its chlorophenol | | | | |
| 26 | 71184 | L1210 | IPIV | 1 | 0.10 | 158-200 | 0/6-1/6 |
| 27 | 71184 | P388 | IPIV | 1 | 0.05-0.20 | 191-263 | 0/6-4/6 |
| 28 | 71184 | P388 | IP-ORAL | 1-5 | 0.08 | 100 | — |
| 29 | 73903 | L1210 | IPIV | 1 | 0.20 | 200-213 | 0/6-1/6 |
| 30 | 73903 | P388 | IPIV | 1 | 0.20 | 242 | 1/6-3/6 |
| 31 | 73903 | P388 | IP-ORAL | 1-5 | 0.16 | 105 | — |
| | | | U-73975 and its chlorophenol | | | | |
| 32 | 73975 | L1210 | IPIV | 1 | 0.05-0.10 | 163-243 | 0/6-2/6 |
| 33 | 73975 | P388 | IPIV | 1 | 0.05-0.10 | 200-230 | 0/6-2/6 |
| 34 | 73896 | L1210 | IPIV | 1 | 0.05-0.20 | 163-213 | 0/6-2/6 |
| 35 | 73896 | P388 | IPIV | 1 | 0.10-0.20 | 232-240 | 0/6-1/6 |
| | | | CC-1065 | | | | |
| 36 | 56314 | P388 | IPIP | 1,5,9 | 0.01-0.05 | 123-168 | |

*These are the most active compounds. However, with 3 or more 30-day survivors a median day of death for a 6 animal group cannot be calculated.

TABLE 2

1. U-71184 adduct

Cpd #1

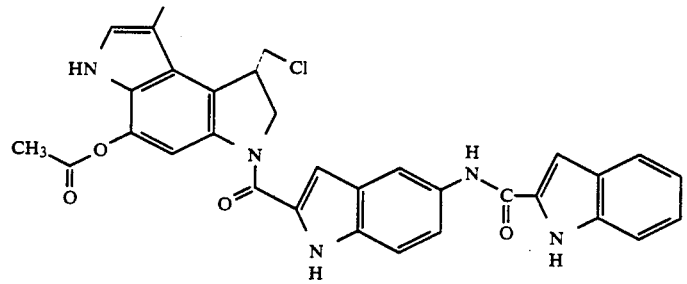

2. U-73975 adducts

TABLE 2-continued
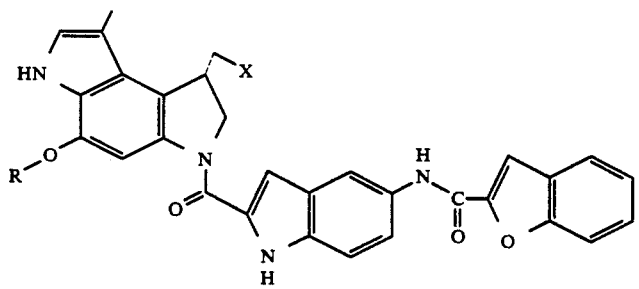
| Cpd # | X | R |
|---|---|---|
| 2A | Cl | $CH_3CO$ |
| 2B | Cl | $CH_3(CH_2)_4CO$ |
| 2C | Cl | $C_6H_5CO$ |
| 2D | Cl | $CH_3(CH_2)_{12}CO$ |
| 2E | Cl | $CH_3(CH_2)_8CO$ |
| 2F | Cl | $CH_3(CH_2)_{10}CO$ |
| 6 | $N_3$ | H |
| 2G | Br | $C_6H_5CO$ |
| 10A | Cl | $C_6H_5NHCO-$ |
| 10B | Cl | $CH_3(CH_2)_3NHCO-$ |
| 10C | Cl | $(CH_3)_3CCO-$ |
| 10D | Cl | $4-(CF_3)_2C_6H_4NHCO-$ |
| 10E | Cl | $3,5-(CH_3)_2C_6H_3NHCO-$ |
| 10F | Cl | $4-ClC_6H_4NHCO-$ |
| 10G | Cl | $3,4-(F)_2C_6H_3NHCO-$ |
3. CC-1065 adducts
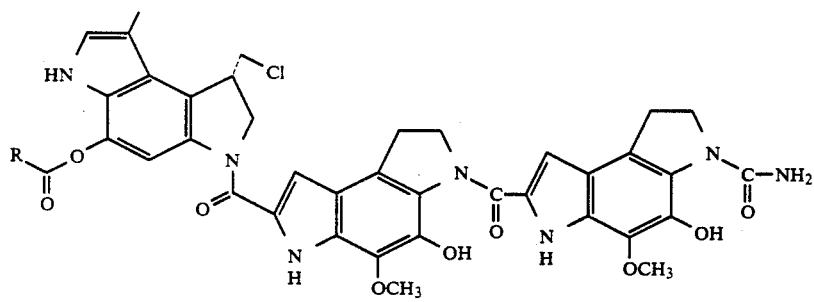
| Cpd # | R |
|---|---|
| 3 | $CH_3(CH_2)_8$ |
| 4 | $CH_3(CH_2)_{12}$ |
| 5 | $CH_3(CH_2)_4$ |
4. U-76074 adducts
Cpd #11a
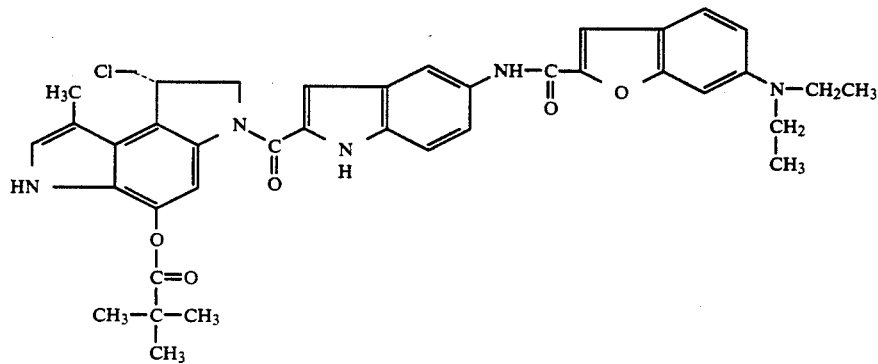

TABLE 2-continued
Cpd #11b
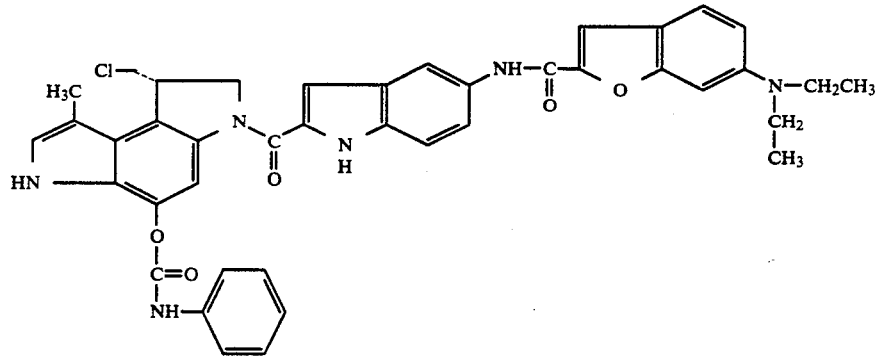
TABLE 3
Cpd # U #
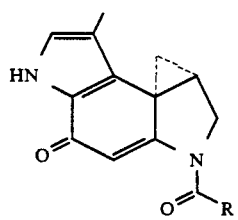
U-71184
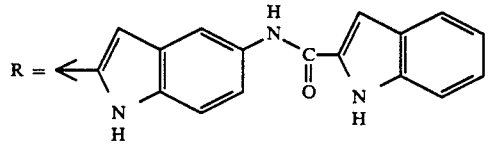
R =
U-73975
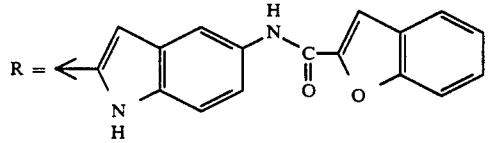
R =
U-56314
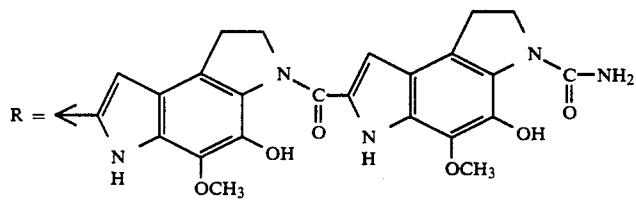
R =
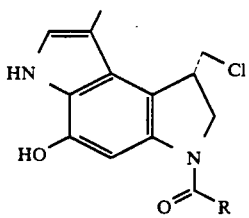
U-73903
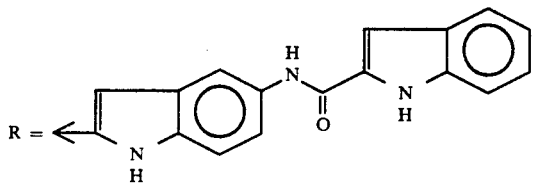
R =

TABLE 3-continued

U-73896

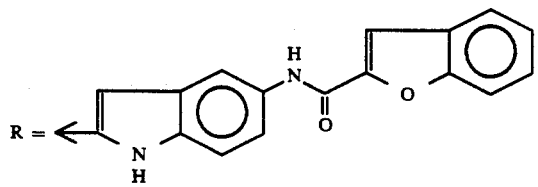

U-76073

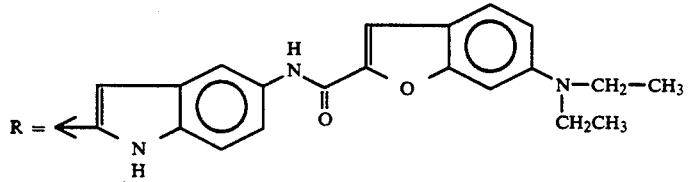

TABLE 4

| U# | Test Tum/Drug | Rt Admin | Days of Dos. | mg/kg | Mi-crom/kg | T/C | Cures |
|---|---|---|---|---|---|---|---|
| 10A | B16 | IPIV | 1 | 0.20 | 0.30 | 163 | — |
| 10A | B16 | IPIV | 1 | 0.20 | 0.30 | 154 | — |
| 10A | L1210 | IPIV | 1 | 0.20 | 0.30 | 250 | 1/6 |
| 10A | L1210 | IPIV | 1 | 0.20 | 0.30 | 213 | — |
| 10B | LLUNG | IPIV | 1,5,9 | 0.10 | 0.16 | 271 | 2/8 |
| 10B | LLUNG | IVIV | 1 | 0.20 | 0.31 | * | 4/8 |
| 10B | L1210 | IPIV | 1 | 0.20 | 0.31 | 200 | — |
| 10C | L1210 | IPIV | 1 | 0.10 | 0.16 | 200 | — |
| 10D | L1210 | IPIV | 1 | 0.30 | 0.41 | 188 | — |
| 10E | L1210 | IPIV | 1 | 0.30 | 0.44 | 200 | — |
| 10F | L1210 | IPIV | 1 | 0.40 | 0.58 | 213 | — |
| 10F | L1210 | IPIV | 1 | 0.40 | 0.58 | 213 | — |
| 11A | L1210 | IPIV | 1 | 0.40 | | 225 | 2/6 |
| 11A | B16 | IPIV | 1 | 0.5 | | 175 | — |
| 11B | L1210 | IPIV | 1 | 0.6 | | 213 | 3/6 |
| 11B | B16 | IPIV | 1 | 0.5 | | 175 | — |

We claim:
1. A compound of formula

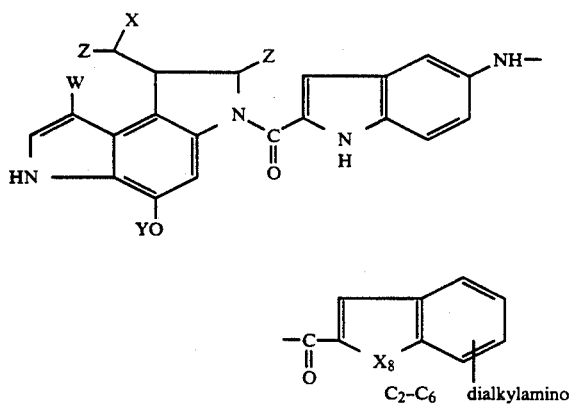

where $X_8$ is —O—, —S— or —NH—;
wherein W is selected from $C_1$-$C_5$ alyl, phenyl or hydrogen;
wherein X is selected from azido, a halogen atom, cyanate, thiocyanate, isocyanate, thioisocyanate, phosphate diester (—PO(OR)$_2$), phosphonyl (—O—PO$_2$R), thiophosphonyl (—O—PSOR), sulfinyl (—O—SOR) or sulfonyl (—O—SO$_2$R);
wherein Y is selected from —C(O)R, —C(S)R, —C(O)OR$_1$, —S(O)$_2$R$_1$, —C(O)NR$_2$R$_3$, —C(S)NR$_2$R$_3$, or —C(O)NHSO$_2$R$_4$;
wherein Z is selected from the group consisting of $C_1$-$C_5$ alkyl, phenyl or hydrogen;
wherein R is selected from the group consisting of $C_1$-$C_{20}$ alkyl; $C_2$-$C_6$ alkenyl; $C_2$-$C_6$ alkynyl; phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro; naphthyl optionally substituted with one or two $C_1$-$C_4$ alkyl, $C_1$-$C_3$ alkoxy, halo, trifluoromethyl, $C_2$-$C_6$ dialkylamino, $C_1$-$C_3$ alkylthio or nitro;
wherein R$_1$ is selected from $C_1$-$C_{20}$ alkyl or phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro;
wherein R$_2$ and R$_3$, being the same or different, are selected from hydrogen, $C_1$-$C_{20}$ alkyl or phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro; with the proviso that both R$_2$ and R$_3$ cannot be phenyl or substituted phenyl; and
wherein R$_4$ is selected from $C_1$-$C_{10}$ alkyl; phenyl optionally substituted with one, two or three $C_1$-$C_4$ alkyl, $C_1$-$C_3$ alkoxy, halo, $C_1$-$C_{alkylthio, trifluoromethyl}$, $C_2$-$C_6$ dialkylamino, or nitro; naphthyl optionally substituted with one or two $C_1$-$C_4$ alkyl, $C_1$-$C_3$ alkoxy, halo, trifluoromethyl, $C_2$-$C_6$ dialkylamino, $C_1$-$C_3$ alkylthio or nitro.

2. A compound according to claim 1 wherein Y is selected from
—COR wherein R is selected from $C_1$-$C_{10}$ alkyl or phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro; —C(O)NHSO$_2$R$_4$; or —C(O)NR$_2$R$_3$.

3. A compound according to claim 1 wherein W is methyl.

4. A compound according to claim 3 wherein Z is hydrogen.

5. A compound according to claim 2 where W is methyl and Z is hydrogen.

6. A compound according to claim 1 where W is methyl, X is chloro and Z is hydrogen.

7. A compound according to claim 30 where X$_8$ is —O—.

8. A compound according to claim 7 wherein Y is selected from —COR wherein R is selected from $C_1$-$C_{10}$ alkyl or phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro;

—C(O)NHSO$_2$R$_4$; or —C(O)NR$_2$R$_3$.

9. A compound according to claim 7 where W is methyl.

10. A compound according to claim 9 where Z is hydrogen.

11. A compound according to claim 8 where W is methyl and Z is hydrogen.

12. A compound according to claim 7 where W is methyl, X is chloro and Z is hydrogen.

13. A compound of claim 30, having the 1(S)-configuration of the stereoisomer of

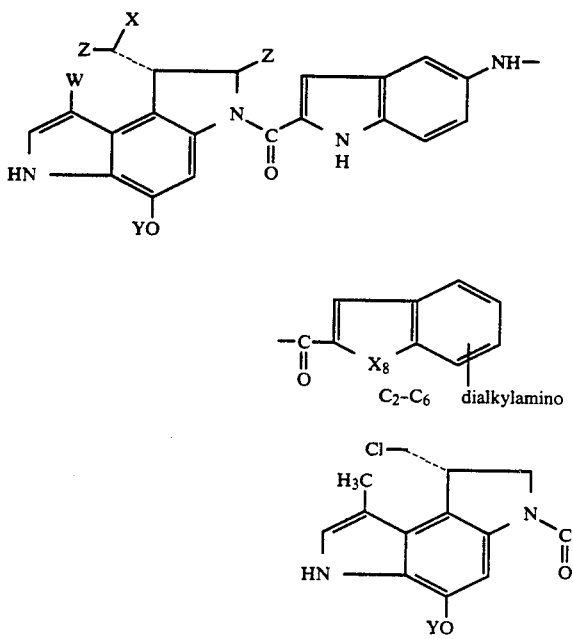

where $X_8$ is —O—, —S— or —NH—;
wherein W is selected from $C_1$-$C_5$ alkyl, phenyl or hydrogen;
wherein X is selected from azido, a halogen atom, cyanate, thiocyanate, isocyanate, thioisocyanate, phosphate diester (—PO(OR)$_2$), phosphonyl (—O—PO$_2$R), thiophosphonyl (—O—PSOR), sulfinyl (—O—SOR) or sulfonyl (—O—SO$_2$R);
wherein Y is selected from —C(O)R, —C(S)R, —C(O)OR$_1$, —S(O)$_2$R$_1$, —C(O)NR$_2$R$_3$, —C(S)NR$_2$R$_3$, or —C(O)NHSO$_2$R$_4$;
wherein Z is selected from the group consisting of $C_1$-$C_5$ alkyl, phenyl or hydrogen;
wherein R is selected from the group consisting of $C_1$-$C_{20}$ alkyl; $C_2$-$C_6$ alkenyl; $C_2$-$C_6$ alkynyl; phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro; naphthyl optionally substituted with one or two $C_1$-$C_4$ alkyl, $C_1$-$C_3$ alkoxy, halo, trifluoromethyl, $C_2$-$C_6$ dialkylamino, $C_1$-$C_3$ alkylthio or nitro;

wherein $R_1$ is selected from $C_1$-$C_{20}$ alkyl or phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro;

wherein $R_2$ and $R_3$, being the same or different, are selected from hydrogen, $C_1$-$C_{20}$ alkyl, or phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro; with the proviso that both $R_2$ and $R_3$ cannot be phenyl or substituted phenyl; and wherein $R_4$ is selected from $C_1$-$C_{10}$ alkyl; phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro; naphthyl optionally substituted with one or two $C_1$-$C_4$ alkyl, $C_1$-$C_3$ alkoxy, halo, trifluoromethyl, $C_2$-$C_6$ dialkylamino, $C_1$-$C_3$ alkylthio or nitro.

14. A compound according to claim 13 wherein Y is selected from
—COR wherein R is selected from $C_1$-$C_{10}$ alkyl or phenyl optionally substituted with one, two or three $C_1$-$C_4$ alkyl, $C_1$-$C_3$ alkoxy, halo, $C_1$-$C_3$ alkylthio, trifluoromethyl, $C_2$-$C_6$ dialkylamino, or nitro;
—C(O)NHSO$_2$R$_4$; or —C(O)NR$_2$R$_3$.

15. A compound according to claim 13 where W is methyl, X is chloro and Z is hydrogen.

16. A compound according to claim 15 where $X_8$ is —O—.

17. A compound according to claim 16 having the formula

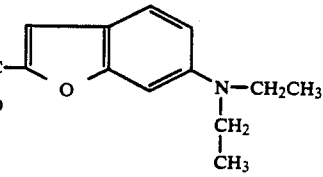

18. A compound according to claim 17 wherein Y is selected from
—COR wherein R is selected from $C_1$-$C_{10}$ alkyl or phenyl optionally substituted with one, two or three $C_1$-$C_4$ alkyl, $C_1$-$C_3$ alkoxy, halo, $C_1$-$C_3$ alkylthio, trifluoromethyl, trifluoromethyl, $C_2$-$C_6$ dialkylamino, or nitro;
—C(O)NHSO$_2$R$_4$; or —C(O)NR$_2$R$_3$.

19. A compound according to claim 17 selected from the group consisting of
(S)-8-(chloromethyl)-6-[[5-[[[6-(diethylamino)-2-benzofuranyl]carbonyl]amino]-1H-indol-2-yl]carbonyl]-3,6,7,8-tetrahydro-1-methylbenzo[1,2-b4,5-b']dipyrrol-4-yl ester, 2,2-dimethyl-propanoic acid (Cpd #11A); or (S)-N-[2[[1-(chloromethyl)-1,6-dihydro-8-methyl-5-[[(phenylamino)carbonyl]oxy]benzo[1,2,-b4,3-b']dipyrrol-3-(2H)-yl]carbonyl]-1H-indol-5-yl]-6-(diethylamino)-2-benzofurancarboxamide (Cpd #11B).

20. (S)-N-[2-[[1-(chloromethyl)-1,6-dihydro-8-methyl-5-[[(phenylamino)carbonyl]oxy]benzo[1,2,-b 4,3-b']dipyrrol-3(2H)-yl]carbonyl]-1H-indol-5-yl]-6-(diethylamino)-2-benzofurancarboxamide.

* * * * *